US005661128A

United States Patent [19]
Cortese et al.

[11] Patent Number: 5,661,128
[45] Date of Patent: Aug. 26, 1997

[54] PEPTIDE INHIBITORS OF FARNESYL-PROTEIN TRANSFERASE

[75] Inventors: Richardo Cortese, Rome, Italy; Jackson B. Gibbs, Calfont, Pa.; Antonello Pessi, Rome; Andrew Wallace, Ariccia, both of Italy

[73] Assignees: Merck & Co. Inc., Rahway, N.J.; Istituto Di Ricerche Di Biologia Molecolare (IRBM), Pomezia, Italy

[21] Appl. No.: 459,885

[22] Filed: Jun. 2, 1995

[30] Foreign Application Priority Data

Sep. 28, 1994 [IT] Italy ........................... 94000620

[51] Int. Cl.$^6$ ............................................ A61K 38/00
[52] U.S. Cl. ............................................ 514/18; 530/330
[58] Field of Search ........................ 514/18; 530/330

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,326,773 | 7/1994 | De Solms et al. | 514/336 |
| 5,340,828 | 8/1994 | Graham et al. | 514/357 |
| 5,352,705 | 10/1994 | Deana et al. | 514/630 |

FOREIGN PATENT DOCUMENTS

| | | |
|---|---|---|
| 0 456 180 A1 | 11/1991 | European Pat. Off. . |
| 0 618 221 A2 | 10/1994 | European Pat. Off. . |
| WO91/16340 | 10/1991 | WIPO . |
| WO94/09766 | 10/1992 | WIPO . |
| WO94/10138 | 10/1992 | WIPO . |
| WO95/11917 | 5/1995 | WIPO . |
| 9610037 | 4/1996 | WIPO . |

OTHER PUBLICATIONS

Gibbs, J.B. et al., "Selective Inhibition of Farnesyl–Protein Transferase Blocks Ras Processing in Vivo", The Journal of Biological Chemistry, vol. 268, No. 11, pp. 7617–7620 (1993).

Goldstein, J.L. et al., "Nonfarnesylated Tetrapeptide Inhibitors of Protein Farnesyltransferase", The Journal of Biological Chemistry, vol. 266, No. 24 pp. 15575–15578 (1991).

James, G.L. et al., "Benzodiazepine Peptidomimetic BZA–5B Interrupts the MAP Kinase Activation Pathway in H–Ras–transformed Rat–1 Cells, but Not in Untransformed Cells", The Journal of Biological Chemistry, vol. 269, No. 44, pp. 27705–27714 (1994).

James, G.L. et al., "Benzodiazepine Peptidomimetics: Potent Inhibitors of Ras Farnesylation in Animal Cells", Science, vol. 260, pp. 1937–1942 (1993).

Kohl, N.E. et al., "Selective Inhibition of Ras–Dependent Transformation by a Farnesyltransferase Inhibitor", Science, vol. 260 pp. 1934–1937 (1993).

Kohl, N.E. et al., "Protein Farnesyltransferase Inhibitors Block the Growth of Ras–Dependent Tumors in Nude Mice", Proc. Natl. Acad. Sci. USA Med. Sci., vol. 91 pp. 9141–9145 (1994).

Pompliano, D.L. et al., "Steady–State Kinetic Mechanism of Ras Farnesyl:Protein Transferase, Biochemistry", vol. 31, pp. 3800–3807 (1992).

James, G.L. et al., "Polylsine and CVIM Sequences of K–Ras B Dictate Specificity of Prenylation an Confer Resistance to Benzodiazepine Peptidomimetic In Vito", The Journal of Biological Chemistry, vol. 270, No. 11 pp. 6221–6226 (1995).

*Primary Examiner*—Cecilia J. Tsang
*Assistant Examiner*—C. Delacroix-Muirheid
*Attorney, Agent, or Firm*—Valerie J. Camara; Mark R. Daniel

[57] ABSTRACT

The present invention is directed to tetrapeptides which inhibit farnesyl-protein transferase (FPTase) and the farnesylation of the oncogene protein Ras. The invention is further directed to a method of treating cancer with tetrapeptide inhibitors of farnesyl protein transferase, as well as pharmaceutical formulations useful for this method of treatment.

37 Claims, No Drawings

PEPTIDE INHIBITORS OF FARNESYL-PROTEIN TRANSFERASE

RELATED APPLICATIONS

This application claims priority under 35 U.S.C. 119 from Italian patent application number 94000620 filed on Sep. 28, 1994.

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989)). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et at., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87: 7541–7545 (1990)).

Farnesyl-protein transferase activity may be reduced or completely inhibited by adjusting the dose of an inhibitory compound. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of Ras, and other cellular proteins, with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et al., ibid; Reiss et al., *PNAS*, 88:732–736 (1991)). CAAX tetrapeptides may inhibit Ras farnesylation while serving as alternate substrates for the Ras farnesyl-transferase enzyme, or may be purely competitive inhibitors (U.S. Pat. No. 5,141,851, University of Texas).

Recently, it has been demonstrated that certain inhibitors of farnesyl-protein transferase selectively block the processing of Ras oncoprotein intracellularly (N. E. Kohl et al., *Science*, 260:1934–1937 (1993) and G. L. James et al., *Science*., 260:1937–1942 (1993). Furthermore, these inhibitors modify the malignant prototype of Ras-transformed cells.

It is, therefore, an object of this invention to develop a compound which will inhibit farnesyl-protein transferase and the farnesylation of the oncogene protein Ras. It is a further object of this invention to develop a compound which does not contain a Cys residue, and thus will not be subject to the metabolic liabilities associated with this amino acid residue.

It is also the object of the invention to develop chemotherapeutic compositions containing the compounds of this invention, as well as the methods for producing the compounds of this invention.

SUMMARY OF THE INVENTION

The present invention includes compounds which inhibit farnesyl-protein transferase and the farnesylation of the oncogene protein Ras chemotherapeutic compositions containing the compounds of this invention, and methods for using the compounds of this invention as chemotherapeutic agents.

The compounds of this invention are illustrated by the Formula I:

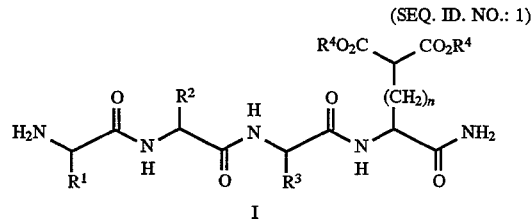

(SEQ. ID. NO.: 1)

I

DETAILED DESCRIPTION OF THE INVENTION

The tetrapeptide compounds of this invention are useful in the inhibition of farnesyl-protein transferase and the farnesylation of the oncogene protein Ras. An embodiment of this invention is the tetrapeptide represented by Formula I:

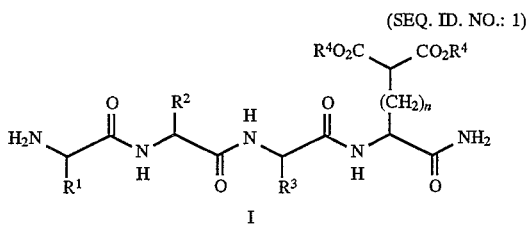

(SEQ. ID. NO.: 1)

I or the pharmaceutically acceptable salts, hydrates, esters or amides thereof, wherein:

n is: 0 to 4, $R^1$ and $R^3$ independently are $C_{0-4}$ alkyl, substituted with substituents selected from the group consisting of:
  a) aryl, which is defined as phenyl or naphthyl, unsubstituted or substituted with one, two, three or four substituents selected from the group consisting of:
     i) F,
     ii) Cl,
     iii) Br,
     iv) nitro,
     v) cyano,
     vi) $C_{1-8}$ alkoxy,
     vii) $C_{1-8}$ alkylthio,
     viii) $C_{1-8}$ alkylsulfonyl,
     ix) sulfamoyl, or
     x) $C_{1-8}$ alkyl; or
  b) heteroaryl, which is defined as indolyl, imidazolyl or pyridyl, unsubstituted or substituted with one, two, three or four substituents selected from the group consisting of:
     i) F,
     ii) Cl,
     iii) Br,
     iv) nitro,
     v) cyano,
     vi) $C_{1-8}$ alkoxy,
     vii) $C_{1-8}$ alkylthio,
     viii) $C_{1-8}$ alkylsulfonyl,
     ix) sulfamoyl, or
     x) $C_{1-8}$ alkyl;

$R^2$ is: $C_{0-6}$ alkyl, which is unsubstituted or substituted with a substituent selected from the group consisting of:
  a) unsubstituted or substituted aryl, as defined in $R^1$(a),
  b) unsubstituted or substituted heteroaryl, as defined in $R^1$(b),
  c) $C_{3-8}$ cycloalkyl,
  d) $C_{1-8}$ alkylthio,
  e) $C_{1-8}$ alkylsulfonyl,
  f) $C_{1-8}$ alkoxy, or
  g) aryl $C_{1-8}$ alkyl sulfonyl; and $R^4$ is: H.

A subclass of this embodiment of the invention is the tetrapeptide represented by Formula I:

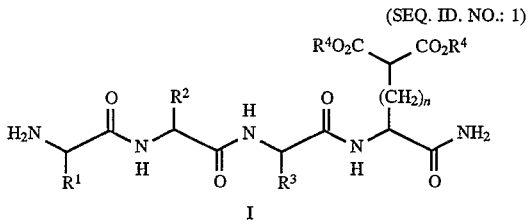

(SEQ. ID. NO.: 1)

I or the pharmaceutically acceptable salts, hydrates, esters or amides thereof, wherein:

n is: 0 to 4;

$R^1$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

$R^2$ is: $C_{0-6}$ alkyl, which is unsubstituted or substituted with a substituent selected from the group consisting of:
  a) aryl, which is defined as phenyl or naphthyl, unsubstituted or substituted with one, two, three or four substituents selected from the group consisting of:
     i) F,
     ii) Cl,
     iii) Br,
     iv) nitro,
     v) cyano,
     vi) $C_{1-8}$ alkoxy,
     vii) $C_{1-8}$ alkylthio,
     viii) $C_{1-8}$ alkylsulfonyl,
     ix) sulfamoyl, or
     x) $C_{1-8}$ alkyl;
  b) heteroaryl, which is defined as indolyl, imidazolyl, or pyridyl, unsubstituted or substituted with one, two, three or four substituents selected from the group consisting of:
     i) F,
     ii) Cl,
     iii) Br,
     iv) nitro,
     v) cyano,
     vi) $C_{1-8}$ alkoxy,
     vii) $C_{1-8}$ alkylthio,
     viii) $C_{1-8}$ alkylsulfonyl,
     ix) sulfamoyl, or
     x) $C_{1-8}$ alkyl;
  c) $C_{3-8}$ cycloalkyl,
  d) $C_{1-8}$ alkylthio,
  e) $C_{1-8}$ alkylsulfonyl,
  f) $C_{1-8}$ alkoxy, or
  g) aryl $C_{1-8}$ alkyl sulfonyl;

$R^3$ is: $C_{0-4}$ alkyl, which is substituted with a substituent selected from the group consisting of:
  a) unsubstituted or substituted aryl, which is as defined in $R^2$(a),
  b) unsubstituted or substituted heteroaryl, which is as defined in $R^2$(b); and $R^4$ is: H.

A second subclass of the first embodiment of this invention is the tetrapeptide represented by Formula I:

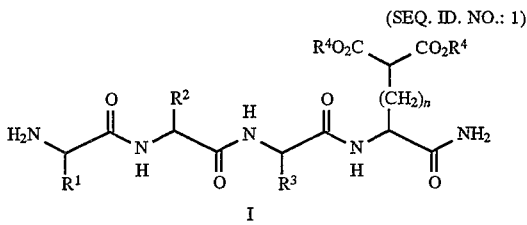

(SEQ. ID. NO.: 1)

I or the pharmaceutically acceptable salts, hydrates, esters or amides thereof, wherein:

n is: 0 to 4;

$R^1$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide;

$R^3$ is: $C_{0-4}$ alkyl, which is substituted with a substituent selected from the group consisting of:
  a) aryl, which is defined as phenyl or naphthyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy,
    vii) $C_{1-8}$ alkylthio,
    viii) $C_{1-8}$ alkylsulfonyl,
    ix) sulfamoyl, or
    x) $C_{1-8}$ alkyl; or
  b) heteroaryl, which is defined as indolyl, imidazolyl or pyridyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy,
    vii) $C_{1-8}$ alkylthio,
    viii) $C_{1-8}$ alkylsulfonyl,
    ix) sulfamoyl, or
    x) $C_{1-8}$ alkyl; and $R^4$ is: H.

A third subclass of the first embodiment of this invention is the tetrapeptide represented by Formula I:

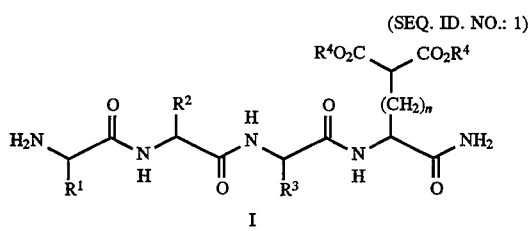

(SEQ. ID. NO.: 1)

I or the pharmaceutically acceptable salts, hydrates, esters or amides thereof, wherein:

n is: 0 to 4;

$R^1$ and $R^3$ independently are: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide; and $R^4$ is: H.

A second embodiment of this invention is a tetrapeptide represented by Formula I:

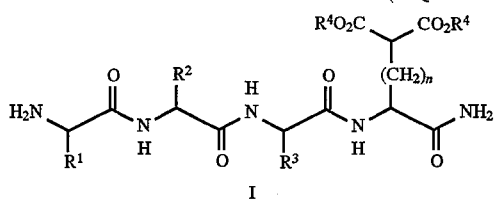

(SEQ. ID. NO.: 1)

I wherein:

n is: 0 to 4;

$R^1$ is: 3-indolylmethyl;

$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide;

$R^3$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl; and $R^4$ is: H.

A subclass of the second embodiment of this invention the tetrapeptide represented by Formula I:

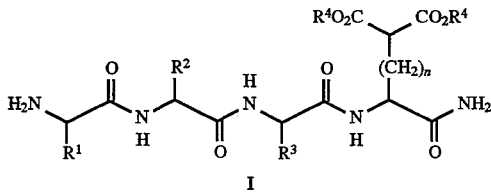

(SEQ. ID. NO.: 1)

I wherein:

n is: 0 to 4;

$R^1$ is: 3-indolylmethyl;

$R^2$ is: 3-indolylmethyl, benzyl, or 3-thiabutyl;

$R^3$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl; and $R^4$ is: H.

A second subclass of the second embodiment of this invention is the tetrapeptide represented by Formula I:

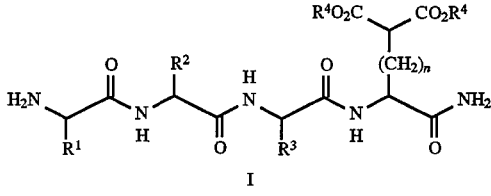

(SEQ. ID. NO.: 1)

I wherein:

n is: 0 to 4;

$R^1$ is: 3-indolylmethyl;

$R^2$ is: 3-indolylmethyl, benzyl, or 3-thiabutyl;

$R^3$ is: 3-indolylmethyl, 4-chlorobenzyl, or benzyl; and $R^4$ is: H.

A third subclass of the second embodiment of this invention is the tetrapeptide represented by Formula I:

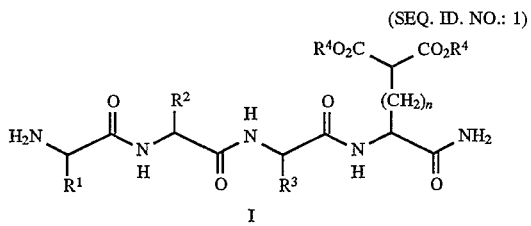

(SEQ. ID. NO.: 1)

I wherein:

n is: 1;

R$^1$ is: 3-indolylmethyl;

R$^2$ is: 3-indolylmethyl, benzyl, or 3-thiabutyl;

R$^3$ is: 3-indolylmethyl, 4-chlorobenzyl, or benzyl; and

R$^4$ is: H.

The preferred compounds of this subclass of the invention are:

D-Tryptophyl-D-phenylalanyl-D-phenylalanyl-L-γ-carboxyglutamyl amide; (SEQ.ID.NO.: 2)

D-Tryptophyl-D-phenylalanyl-D-tryptophyl-L-γ-carboxyglutamyl amide; (SEQ.ID.NO.: 3)

D-Tryptophyl-D-phenylalanyl-D-p-chlorophenylalanyl-L-γ-carboxyglutamyl amide; (SEQ.ID.NO.: 4)

D-Tryptophyl-D-phenylalanyl-L-p-chlorophenylalanyl-L-γ-carboxyglutamyl amide; (SEQ.ID.NO.: 5)

D-Tryptophyl-D-tryptophyl-D-phenylalanyl-L-γ-carboxyglutamyl amide; (SEQ.ID.NO.: 6)

D-Tryptophyl-D-tryptophyl-D-tryptophyl-L-γ-carboxyglutamyl amide; (SEQ.ID.NO.: 7)

D-Tryptophyl-D-tryptophyl-D-p-chlorophenylalanyl-L-γ-carboxyglutamyl amide; (SEQ.ID.NO.: 8)

D-Tryptophyl-D-tryptophyl-L-p-chlorophenylalanyl-L-γ-carboxyglutamyl amide; (SEQ.ID.NO.: 9)

D-Tryptophyl-D-methioninyl-D-phenylalanyl-L-γ-carboxyglutamyl amide; (SEQ.ID.NO.: 10)

D-Tryptophyl-D-methioninyl-D-tryptophyl-L-γ-carboxyglutamyl amide; (SEQ.ID.NO.: 11)

D-Tryptophyl-D-methioninyl-D-p-chlorophenylalanyl-L-γ-carboxyglutamyl amide; (SEQ.ID.NO.: 12)

D-Tryptophyl-D-methioninyl-L-p-chlorophenylalanyl-L-γ-carboxyglutamyl amide; (SEQ.ID.NO.: 13)

D-Tryptophyl-L-tryptophyl-D-phenylalanyl-L-γ-carboxyglutamyl amide; (SEQ.ID.NO.: 14)

D-Tryptophyl-L-tryptophyl-D-tryptophyl-L-γ-carboxyglutamyl amide; (SEQ.ID.NO.: 15)

D-Tryptophyl-L-tryptophyl-D-p-chlorophenylalanyl-L-γ-carboxyglutamyl amide; and (SEQ.ID.NO.: 16)

D-Tryptophyl-L-tryptophyl-L-p-chlorophenylalanyl-L-γ-carboxyglutamyl amide. (SEQ.ID.NO.: 17)

The more preferred compounds of this subclass of the invention are

D-Tryptophyl-D-phenylalanyl-D-p-chlorophenylalanyl-L-γ-carboxyglutamyl amide; (SEQ.ID.NO.: 4)

D-Tryptophyl-D-tryptophyl-D-p-chlorophenylalanyl-L-γ-carboxyglutamyl amide; (SEQ.ID.NO.: 8)

D-Tryptophyl-D-methioninyl-D-phenylalanyl-L-γ-carboxyglutamyl amide; and (SEQ.ID.NO.: 10)

D-Tryptophyl-D-methioninyl-D-p-chlorophenylalanyl-L-γ-carboxyglutamyl amide. (SEQ.ID.NO.: 12)

A third embodiment of this invention is a tetrapeptide represented by Formula I:

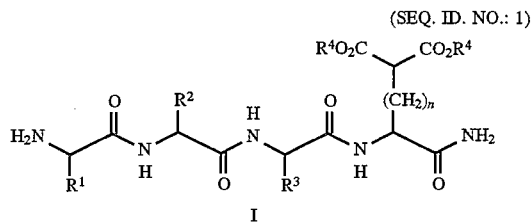

(SEQ. ID. NO.: 1)

I or the pharmaceutically acceptable salts, hydrates, esters or amides thereof, wherein:

n is: 0 to 4,

R$^1$ and R$^3$ independently are $C_{0-4}$ alkyl, substituted with substituents selected from the group consisting of:
  a) aryl, which is defined as phenyl or naphthyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy,
    vii) $C_{1-8}$ alkylthio,
    viii) $C_{1-8}$ alkylsulfonyl,
    ix) sulfamoyl, or
    x) $C_{1-8}$ alkyl; or
  b) heteroaryl, which is defined as indolyl, imidazolyl or pyridyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy,
    vii) $C_{1-8}$ alkylthio,
    viii) $C_{1-8}$ alkylsulfonyl,
    ix) sulfamoyl, or
    x) $C_{1-8}$ alkyl;

R$^2$ is: $C_{0-6}$ alkyl, which is unsubstituted or substituted with a substituent selected from the group consisting of:
  a) unsubstituted or substituted aryl, as defined in R$^1$ (a),
  b) unsubstituted or substituted heteroaryl, as defined in R$^1$(b),
  c) $C_{3-8}$ cycloalkyl,
  d) $C_{1-8}$ alkylthio,
  e) $C_{1-8}$ alkylsulfonyl,
  f) $C_{1-8}$ alkoxy, or
  g) aryl $C_{1-8}$ alkyl sulfonyl; and R$^4$ is:
  a) $C_{1-6}$ alkyl,
  b) aryl, which is as defined in R$^1$(a),
  c) $C_{1-6}$ alkylaryl, where aryl is as defined in R$^1$(a), or
  d)

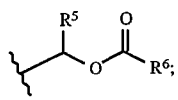

R$^5$ is: H or $C_{1-6}$ alkyl; and

R$^6$ is: $C_{1-6}$ alkyl.

A subclass of this embodiment of the invention is the tetrapeptide represented by Formula I:

9

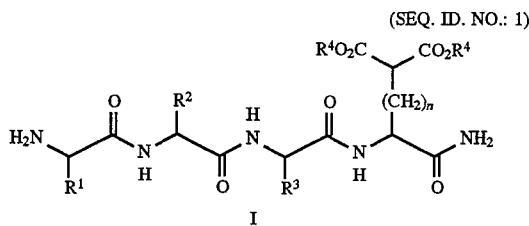

(SEQ. ID. NO.: 1)

I or the pharmaceutically acceptable salts, hydrates, esters or amides thereof, wherein:

n is: 0 to 4;

$R^1$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

$R^2$ is: $C_{0-6}$ alkyl, which is unsubstituted or substituted with a substituent selected from the group consisting of:
- a) aryl, which is defined as phenyl or naphthyl, unsubstituted or substituted with one, two, three or four substituents selected from the group consisting of:
  - i) F,
  - ii) Cl,
  - iii) Br,
  - iv) nitro,
  - v) cyano,
  - vi) $C_{1-8}$ alkoxy,
  - vii) $C_{1-8}$ alkylthio,
  - viii) $C_{1-8}$ alkylsulfonyl,
  - ix) sulfamoyl, or
  - x) $C_{1-8}$ alkyl;
- b) heteroaryl, which is defined as indolyl, imidazolyl, or pyridyl, unsubstituted or substituted with one, two, three or four substituents selected from the group consisting of:
  - i) F,
  - ii) Cl,
  - iii) Br,
  - iv) nitro,
  - v) cyano,
  - vi) $C_{1-8}$ alkoxy,
  - vii) $C_{1-8}$ alkylthio,
  - viii) $C_{1-8}$ alkylsulfonyl,
  - ix) sulfamoyl, or
  - x) $C_{1-8}$ alkyl;
- c) $C_{3-8}$ cycloalkyl,
- d) $C_{1-8}$ alkylthio,
- e) $C_{1-8}$ alkylsulfonyl,
- f) $C_{1-8}$ alkoxy, or
- g) aryl $C_{1-8}$ alkyl sulfonyl;

$R^3$ is: $C_{0-4}$ alkyl, which is substituted with a substituent selected from the group consisting of:
- a) unsubstituted or substituted aryl, which is as defined in $R^2$(a),
- b) unsubstituted or substituted heteroaryl, which is as defined in $R^2$(b); and $R^4$ is:
- a) $C_{1-6}$ alkyl,
- b) aryl, which is as defined in $R^2$(a),
- c) $C_{1-6}$ alkylaryl, where aryl is as defined in $R^2$(a), or

10 d)

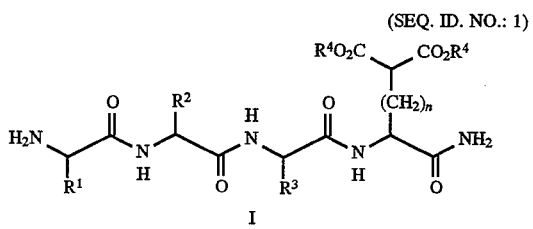

$R^5$ is: H or $C_{1-6}$ alkyl; and $R^6$ is: $C_{1-6}$ alkyl.

A second subclass of the third embodiment of this invention is the tetrapeptide represented by Formula I:

(SEQ. ID. NO.: 1)

I or the pharmaceutically acceptable salts, hydrates, esters or amides thereof, wherein:

n is: 0 to 4;

$R^1$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide;

$R^3$ is: $C_{0-4}$ alkyl, which is substituted with a substituent selected from the group consisting of:
- a) aryl, which is defined as phenyl or naphthyl, unsubstituted or substituted with one, two, three or four substituents selected from the group consisting of:
  - i) F,
  - ii) Cl,
  - iii) Br,
  - iv) nitro,
  - v) cyano,
  - vi) $C_{1-8}$ alkoxy,
  - vii) $C_{1-8}$ alkylthio,
  - viii) $C_{1-8}$ alkylsulfonyl,
  - ix) sulfamoyl, or
  - x) $C_{1-8}$ alkyl; or
- b) heteroaryl, which is defined as indolyl, imidazolyl or pyridyl, unsubstituted or substituted with one, two, three or four substituents selected from the group consisting of:
  - i) F,
  - ii) Cl,
  - iii) Br,
  - iv) nitro,
  - v) cyano,
  - vi) $C_{1-8}$ alkoxy,
  - vii) $C_{1-8}$ alkylthio,
  - viii) $C_{1-8}$ alkylsulfonyl,
  - ix) sulfamoyl, or
  - x) $C_{1-8}$ alkyl; and $R^4$ is:
- a) $C_{1-6}$ alkyl,
- b) aryl, which is as defined in $R^3$(a),
- c) $C_{1-6}$ alkylaryl, where aryl is as defined in $R^3$(a), or d)

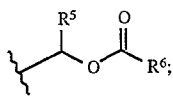

$R^5$ is: H or $C_{1-6}$ alkyl; and
$R^6$ is: $C_{1-6}$ alkyl.

A third subclass of the third embodiment of this invention is the tetrapeptide represented by Formula I:

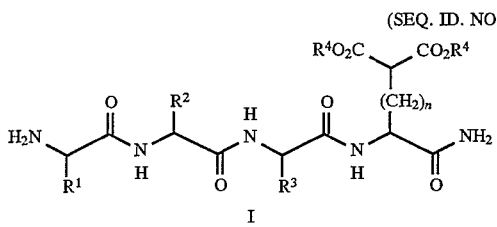

(SEQ. ID. NO.: 1)

or the pharmaceutically acceptable salts, hydrates, esters or amides thereof, wherein:

n is: 0 to 4;

$R^1$ and $R^3$ independently are: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide; and $R^4$ is:
a) $C_{1-6}$ alkyl,
b) aryl, which is as defined in $R^1$(a),
c) $C_{1-6}$ alkylaryl, where aryl is as defined in $R^1$(a), or
d)

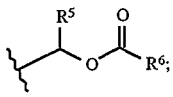

$R^5$ is: H or $C_{1-6}$ alkyl; and
$R^6$ is: $C_{1-6}$ alkyl.

A fourth subclass of the third embodiment of this invention is the tetrapeptide represented by Formula I:

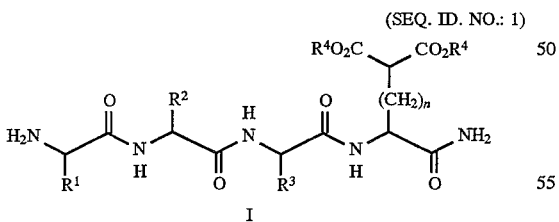

(SEQ. ID. NO.: 1)

wherein:

n is: 0 to 4;

$R^1$ and $R^3$ independently are: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide;

$R^4$ is: $C_{1-6}$ alkyl, or

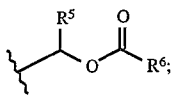

$R^5$ is: H or $C_{1-6}$ alkyl; and
$R^6$ is: $C_{1-6}$ alkyl.

A fourth embodiment of the invention is a tetrapeptide represented by Formula I:

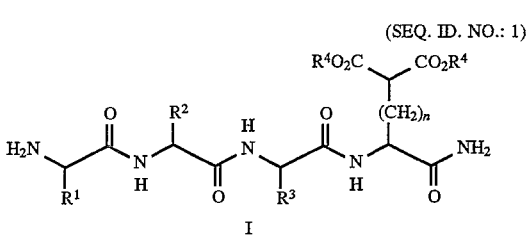

(SEQ. ID. NO.: 1)

wherein:

n is: 0 to 4;

$R^1$ is: 3-indolylmethyl;

$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide;

$R^3$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl; and $R^4$ is: $C_{1-6}$ alkyl, or

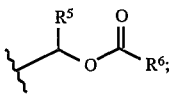

$R^5$ is: H or $C_{1-6}$ alkyl; and
$R^6$ is: $C_{1-6}$ alkyl.

A subclass of the fourth embodiment of this invention is the tetrapeptide represented by Formula I:

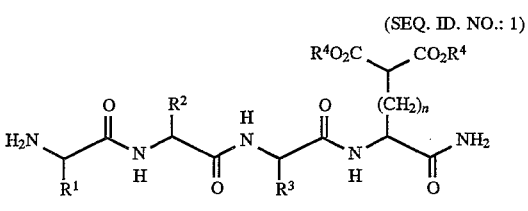

(SEQ. ID. NO.: 1)

wherein:

n is: 0 to 4;

$R^1$ is: 3-indolylmethyl;

$R^2$ is: 3-indolylmethyl, benzyl, or 3-thiabutyl;

$R^3$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl; and $R^4$ is: $C_{1-6}$ alkyl, or

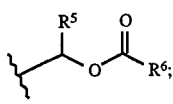

$R^5$ is: H or $C_{1-6}$ alkyl; and
$R^6$ is: $C_{1-6}$ alkyl.

A second subclass of the fourth embodiment of this invention is the tetrapeptide represented by Formula I:

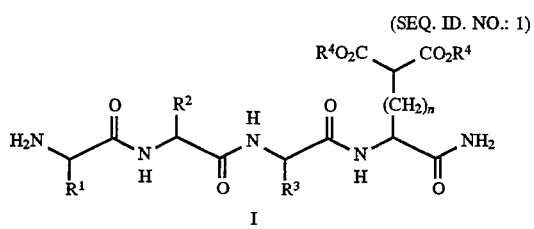

(SEQ. ID. NO.: 1)

wherein:
n is: 0 to 4;
$R^1$ is: 3-indolylmethyl;
$R^2$ is: 3-indolylmethyl, benzyl, or 3-thiabutyl;
$R^3$ is: 3-indolylmethyl, 4-chlorobenzyl, or benzyl; and
$R^4$ is: $C_{1-6}$ alkyl, or

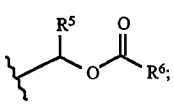

$R^5$ is: H or $C_{1-6}$ alkyl; and
$R^6$ is: $C_{1-6}$ alkyl.

A third subclass of the fourth embodiment of this invention is the tetrapeptide represented by Formula I:

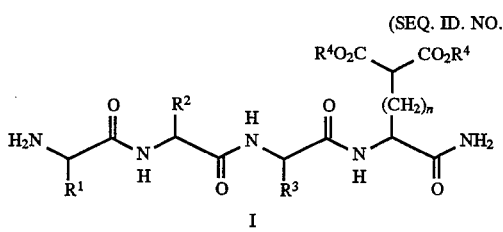

(SEQ. ID. NO.: 1)

wherein:
n is 1;
$R^1$ is: 3-indolylmethyl;
$R^2$ is: 3-indolylmethyl, benzyl, or 3-thiabutyl;
$R^3$ is: 3-indolylmethyl, 4-chlorobenzyl, or benzyl;
$R^4$ is: methyl, ethyl, isopropyl, isobutyl or

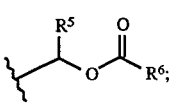

$R^5$ is: H or methyl; and
$R^6$ is: 1,1-dimethylethyl.

The preferred compounds of this subclass of the invention are:

D-Tryptophyl-D-phenylalanyl-D-phenylalanyl-L-γ-carboxyglutamyl amide dimethyl ester; (SEQ.ID.NO.: 18)

D-Tryptophyl-D-phenylalanyl-D-tryptophyl-L-γ-carboxyglutamyl amide dimethyl ester; (SEQ.ID.NO.: 19)

D-Tryptophyl-D-phenylalanyl-D-p-chlorophenylalanyl-L-γ-carboxyglutamyl amide dimethyl ester; (SEQ.ID.NO.: 20)

D-Tryptophyl-D-phenylalanyl-L-p-chlorophenylalanyl-L-γ-carboxyglutamyl amide dimethyl ester; (SEQ.ID.NO.: 21)

D-Tryptophyl-D-tryptophyl-D-phenylalanyl-L-γ-carboxyglutamyl amide dimethyl ester; (SEQ.ID.NO.: 22)

D-Tryptophyl-D-tryptophyl-D-tryptophyl-L-γ-carboxyglutamyl amide dimethyl ester; (SEQ.ID.NO.: 23)

D-Tryptophyl-D-tryptophyl-D-p-chlorophenylalanyl-L-γ-carboxyglutamyl amide dimethyl ester; (SEQ.ID.NO.: 24)

D-Tryptophyl-D-tryptophyl-L-p-chlorophenylalanyl-L-γ-carboxyglutamyl amide dimethyl ester; (SEQ.ID.NO.: 25)

D-Tryptophyl-D-methioninyl-D-phenylalanyl-L-γ-carboxyglutamyl amide dimethyl ester; (SEQ.ID.NO.: 26)

D-Tryptophyl-D-methioninyl-D-tryptophyl-L-γ-carboxyglutamyl amide dimethyl ester; (SEQ.ID.NO.: 27)

D-Tryptophyl-D-methioninyl-D-p-chlorophenylalanyl-L-γ-carboxyglutamyl amide dimethyl ester; (SEQ.ID.NO.: 28)

D-Tryptophyl-D-methioninyl-L-p-chlorophenylalanyl-L-γ-carboxyglutamyl amide dimethyl ester; (SEQ.ID.NO.: 29)

D-Tryptophyl-L-tryptophyl-D-phenylalanyl-L-γ-carboxyglutamyl amide dimethyl ester; (SEQ.ID.NO.: 30)

D-Tryptophyl-L-tryptophyl-D-tryptophyl-L-γ-carboxyglutamyl amide dimethyl ester; (SEQ.ID.NO.: 31)

D-Tryptophyl-L-tryptophyl-D-p-chlorophenylalanyl-L-γ-carboxyglutamyl amide dimethyl ester; and (SEQ.ID.NO.: 32)

D-Tryptophyl-L-tryptophyl-L-p-chlorophenylalanyl-L-γ-carboxyglutamyl amide dimethyl ester. (SEQ.ID.NO.: 33)

The more preferred compounds of this subclass of the invention are:

D-Tryptophyl-D-phenylalanyl-D-p-chlorophenylalanyl-L-γ-carboxyglutamyl amide dimethyl ester; (SEQ.ID.NO.: 20)

D-Tryptophyl-D-tryptophyl-D-p-chlorophenylalanyl-L-γ-carboxyglutamyl amide dimethyl ester; (SEQ.ID.NO.: 24)

D-Tryptophyl-D-methioninyl-D-phenylalanyl-L-γ-carboxyglutamyl amide dimethyl ester; and (SEQ.ID.NO.: 26)

D-Tryptophyl-D-methioninyl-D-p-chlorophenylalanyl-L-γ-carboxyglutamyl amide dimethyl ester. (SEQ.ID.NO.: 28)

Formula I of this invention can also be represented by:

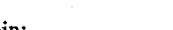

wherein:
$Xaa^1$ is: the N-terminus residue, represented by Formula A:

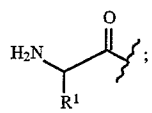

Xaa² is: the second residue of Formula I, represented by Formula B:

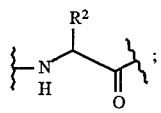

Xaa³ is: the third residue of Formula I, represented by Formula C:

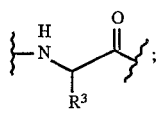

Xaa⁴ is: the C-terminal residue of Formula I, represented by Formula D:

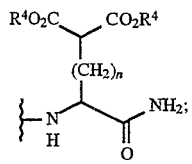

and $Xaa^1$, $Xaa^2$, $Xaa^3$ and $Xaa^4$ are L- or D- natural amino acids, except Cys, or L- or D- unnatural amino acids, as defined below; or the pharmaceutically acceptable salts, hydrates, esters or amides thereof.

In the present invention, the amino acids are listed by the conventional 3-letter abbreviation, as shown below. Unless indicated in the present invention, the substituents for $R^1$ through $R^6$ and the amino acids can have either the L- or D- configuration.

| NATURAL AMINO ACIDS | |
|---|---|
| Alanine | Ala |
| Arginine | Arg |
| Asparagine | Asn |
| Aspartic Acid | Asp |
| Glutamic Acid | Glu |
| Glutamine | Gln |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |
| UNNATURAL AMINO ACIDS | |
| β-Alanine (3-aminopropionic acid) | β-Ala |
| α-Aminobutyric acid | Abu |
| α-Aminoisobutyric acid | αAib |
| γ-Aminobutyric acid | γAbu |
| ε-Aminohexanoic acid | εAhx |
| Cyclohexylalanine | Cha |
| 3,4-dehydro-proline | dhP |

| -continued | |
|---|---|
| γ-Carboxy-glutamic acid | Gla |
| Homo-phenylalanine | Hof |
| Hydroxyproline | Hyp |
| Norvaline | Nva |
| Norleucine | Nle |
| Ornithine | Orn |
| p-Chloro-phenylalanine | Fcl |
| p-Fluoro-phenylalanine | Ffl |
| p-Nitro-phenylalanine | FNO |
| Sarcosine (N-methyl-glycine) | Sar |
| Phenylglycine | Phg |
| 8-Aminooctanoic acid | Aoc |
| (2S)-2,3-Diaminopropionic acid | DAP |
| 5-Aminopentanoic acid (5-Aminovaleric acid) | Ava |
| (3S,4S)-4-Amino-3-hydroxy-6-methylheptanoic acid | Sta |
| 1,2,3,4-Tetrahydroisoquinoline-L-3-carboxylic acid | Tic |
| (3S,4S)-4-Amino-3-hydroxy-5-cyclohexyl-pentanoic acid | ACHPA |
| (3S,4S)-4-Amino-3-hydroxy-5-phenyl-pentanoic acid | AHPPA |

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "aryl" is intended to mean any stable monocyclic, bicyclic or tricyclic carbon ring of up to 7 members in each ring, wherein at least one ring is aromatic. Examples of such aryl elements include phenyl or naphthyl.

The term "heteroaryl", as used herein, represents a stable 5- to 7-membered monocyclic or stable 8- to 11-membered bicyclic or stable 11–15 membered tricyclic heteroaryl ring which is either saturated or unsaturated, and which consists of carbon atoms and from one to four heteroatoms selected from the group consisting of N, O, and $S(O)_m$ (wherein m=0, 1 or 2), and including any bicyclic group in which any of the above-defined heterocyclic rings is fused to a benzene ring. The heteroaryl ring may be attached at any heteroatom or carbon atom which results in the creation of a stable structure. Examples of such heteroaryl elements include imidazolyl, indolyl, or pyridyl.

As used herein, "natural amino acids" are intended to include all amino acids listed as such on page 19; "unnatural amino acids" are intended to include all amino acids listed as such on pages 19 to 20, as well as any substituted natural amino acid.

As used herein, "aromatic amino acids" are intended to include any amino acid, natural or unnatural, which contains at least one ring that is aromatic. Examples of such include, but are not limited to, Trp, Phe, FNO, Fcl, Ffl, Tyr, o-methyl-Tyr, 3-pyridyl-Ala, His, or α[(2-phenyl)ethyl]Gly.

As used herein, "nonpolar amino acids" are intended to include all aliphatic, hydroxyl and sulfur (excluding cys) natural amino acids, as well as unnatural amino acids wherein the α carbon is substituted with a nonpolar substituent. Examples of these amino acids include, but are not limited to, Gly, Ala, Val, Leu, Ile, Ser, Thr, Met, Cha, Nle, or Met-Sulfone The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, and the like.

The pharmaceutically acceptable salts of the present invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, preferably by solid-phase technology. The amino acids used to prepare the tetrapeptides of Formula I are commercially available from Novabiochem, Switzerland; Advanced ChemTech, USA; Neosystem, France; or Bachem, Switzerland. The standard Fmoc-polyamide solid-phase peptide synthesis methodology, as disclosed in Atherton et al., *J. Chem. Soc. Perkin. I*, p. 538–546, (1981), was used to prepare the tetrapeptides of Formula I. The peptides are then purified by reverse-phase high performance liquid chromatography (HPLC).

Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984, or Atherton, E., Logan, C. J. and Sheppard, R. C., J. Chem. Soc. Perkin. Trans. 1, 538, 1981. The teachings of these works are hereby incorporated by reference.

Peptides were prepared with an Applied Biosystems model 430A peptide synthesizer, converted to the corresponding amides by standard procedures, purified by reverse-phase HPLC, and characterized by amino acid analysis and fast atom bombardment mass spectrometry.

Ras proteins used as substrates were expressed in *E. coli* and purified. (Gibbs et al., *Proc. Natl. Acad. Sci. USA*, 85:5026–5030 (1988). Recombinant farnesyl-protein transferase was prepared from *E. coli*. Wild-type human farnesyl-protein transferase was isolated by a modification of an immunoaffinity procedure using the antibody YL1/2 (Stammers et al., *FEBS Lett*. 283., 298–302, 1991). An *E. coli.* cell pellet was resuspended in 50 mM Tris-HCl, pH 7.5, 1 mM EDTA, 1 mM EGTA, 1 mM DTT, 1 mM PMSF, 2 µg/mL leupeptin, 2 mg/mL antipain, and 10 µg/mL aprotinin (approximately 5 g of cells/10 mL solution). The resuspended cells were broken by sonication, and the cell debris was pelleted by centrifugation at 30000 g at 4° C. for 30 min. The soluble fraction was diluted with an equal volume of 0.15M NaCl and 6 mM sodium phosphate, pH 7.2 (1×PBS), and applied at a flow rate of approximately 0.5 mL/min to a 2 mL column of the monoclonal antibody YL1/2 coupled to a cyanogen bromide activated Sepharose (4 mg of antibody/mL of resin). After the protein was loaded onto the column, the column was washed with 10–20 mL of ½×PBS containing 2 mM DTT, 0.1% Tween-20, 1 mM PMSF, 2 µg/mL leupeptin, 2 µg/mL antipain, and 10 µg/mL aprotinin. The column was then washed with 100–200 mL of ½×PBS containing 2 mM DTT. Farnesyl-protein transferase was eluted with 3×3 mL of 5 mM Asp-Phe dipeptide (Sigma), 100 mM Tris-HCl, pH 7.5, and 2 mM DTT. To further purify the farnesyl-protein transferase, protein eluted from the antibody column was chromatographed by HPLC on a Mono Q HR 10/10 column (Pharmacia), where buffer A was 50 mM Tris-HCl, pH 7.5, 5 mM $MgCl_2$, and 5 mM DTT and buffer B was A plus 1M NaCl. The column was run at 1 mL/min with a gradient of 0–20% buffer B, 0–10 min; 20–40% buffer B, 10–40 min; and 40–100% buffer B, 40–60 min. Farnesyl-protein transferase holoenzyme eluted at approximately 30–35% buffer B. Recombinant human farnesyl-protein transferase prepared in this way was of 70–90% purity as estimated by Coomassie blue stained SDS-PAGE. (Omer et al., *Biochemistry.* 32:5169 (1993)).

Polyisoprenylation of Ras-[$^3$H]Farnesyl diphosphate (FPP) (20 Ci/mmol) was purchased from New England Nuclear. Farnesyl-protein transferase activity assays were carried out at 30° C. unless noted otherwise. Farnesyl-protein transferase activity was assayed in 1 nM farnesyl-protein transferase, 100 nM FPP and 100 nM Ras-CVIM as substrates as described (Pompliano et al., *Biochemistry* 31, 3800–3807, 1992). After thermally pre-equilibrating the assay mixture in the absence of enzyme, reactions were initiated by the addition of farnesyl-protein transferase and stopped at timed intervals by the addition of 1M HCl in ethanol (1 mL). The quenched reactions were allowed to stand for 15 minutes (to complete the precipitation process). After adding 2 mL of 100% ethanol, the reactions were vacuum-filtered through Whatmann GF/C filters. The filters were washed four times with 2 mL aliquots of 100% ethanol, mixed with scintillation fluid (10 mL) and then counted in a Beckmann LS3801 scintillation counter.

For inhibition studies, assays were run as described above, except putative inhibitors were added at the concentration indicated, and $IC_{50}$ values were determined with both farnesyl-protein transferase substrates at their $K_M$ concentrations. The $K_M$ for Ras protein substrate having the CAAX sequence, CVIM, is 0.1 nM and the $K_M$ for FPP is 0.1 nM.

In this assay, the claimed tetrapeptides demonstrated the ability to inhibit farnesyl-protein transferase at an $IC_{50}$ concentration of 10 µM or less.

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g. saline, at a pH level e.g. 7.4. The solutions may be introduced into a patient's intramuscular bloodstream by local bolus injection.

When a compound according to this invention is administered to mammals, preferably humans, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

EXAMPLES

Examples provided are intended to assist in a further understanding of the invention. Particular materials employed, species and conditions are intended to be further illustrative of the invention and not limitative of the reasonable scope thereof.

The tetrapeptides used were synthesized according to the methods described above. They were purified by HPLC with a Beckman Ultrasphere ODS (C-18) column, dimensions 250×4.6 mm, particle diameter 5 μm, using the following buffers: A=0.1% TFA in water, B=0.1% TFA in acetonitrile. Upon sample injection the column was developed with a linear gradient from 85% A: 15% B to 50% A: 50% B over 15 min at a flow rate of 1 ml/min. Mass spectrometry data was obtained by Fast Atom Bombardment (FAB) mass spectroscopy using standard conditions.

| Example Number | Sequence Name | HPLC $t_r$ (min.) | Mass Spectroscopy Expected MW/ Observed MW |
|---|---|---|---|
| 1 | trp phe phe Gla | 12.47 | 690/690 |
| 2 | trp phe trp Gla | 12.89 | 710/710 |
| 3 | trp phe fcl Gla | 13.89 | 705/705 |
| 4 | trp phe Fcl Gla | 15.75 | 705/705 |
| 5 | trp trp phe Gla | 13.27 | 710/710 |
| 6 | trp trp trp Gla | 13.45 | 749/749 |
| 7 | trp trp fcl Gla | 14.58 | 744/744 |
| 8 | trp trp Fcl Gla | 15.66 | 744/744 |
| 9 | trp met phe Gla | 11.01 | 655/655 |
| 10 | trp met trp Gla | 11.36 | 694/694 |
| 11 | trp met fcl Gla | 12.62 | 689/689 |
| 12 | trp met Fcl Gla | 14.28 | 689/689 |
| 13 | trp Trp phe Gla | 14.70 | 710/710 |
| 14 | trp Trp trp Gla | 14.65 | 749/749 |
| 15 | trp Trp fcl Gla | 16.02 | 744/744 |
| 16 | trp Trp Fcl Gla | 15.43 | 744/744 |

What is claimed is:

1. A tetrapeptide represented by Formula I:

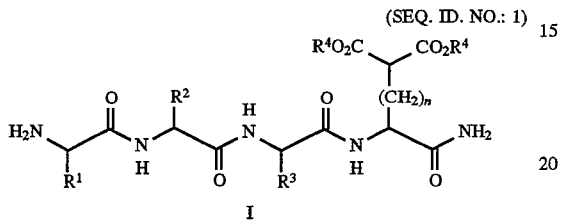

(SEQ. ID. NO.: 1)

I or the pharmaceutically acceptable salts, hydrates, esters or amides thereof, wherein:

n is: 0 to 4, $R^1$ and $R^3$ independently are $C_{0-4}$ alkyl, substituted with substituents selected from the group consisting of:
  a) aryl, which is defined as phenyl or naphthyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy,
    vii) $C_{1-8}$ alkylthio,
    viii) $C_{1-8}$ alkylsulfonyl,
    ix) sulfamoyl, or
    x) $C_{1-8}$ alkyl; or
  b) heteroaryl, which is defined as indolyl, imidazolyl or pyridyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy,
    vii) $C_{1-8}$ alkylthio,
    viii) $C_{1-8}$ alkylsulfonyl,
    ix) sulfamoyl, or
    x) $C_{1-8}$ alkyl;

$R^2$ is: $C_{0-6}$ alkyl, which is unsubstituted or substituted with a substituent selected from the group consisting of:
  a) unsubstituted or substituted aryl, as defined in $R^1$(a),
  b) unsubstituted or substituted heteroaryl, as defined in $R^1$(b),
  c) $C_{3-8}$ cycloalkyl,
  d) $C_{1-8}$ alkylthio,
  e) $C_{1-8}$ alkylsulfonyl,
  f) $C_{1-8}$ alkoxy, or
  g) aryl $C_{1-8}$ alkyl sulfonyl; and $R^4$ is: H.

2. The tetrapeptide as recited in claim 1 represented by Formula I:

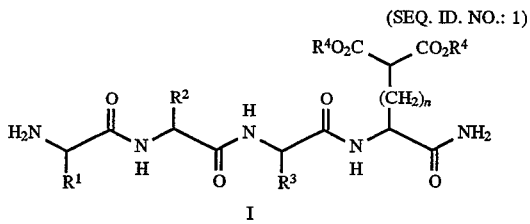

(SEQ. ID. NO.: 1)

I or the pharmaceutically acceptable salts, hydrates, esters or amides thereof, wherein:

n is: 0 to 4;

$R^1$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

$R^2$ is: $C_{0-6}$ alkyl, which is unsubstituted or substituted with a substituent selected from the group consisting of:
  a) aryl, which is defined as phenyl or naphthyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy, o vii) $C_{1-8}$ alkylthio,
    viii) $C_{1-8}$ alkylsulfonyl,
    ix) sulfamoyl, or
    x) $C_{1-8}$ alkyl;
  b) heteroaryl, which is defined as indolyl, imidazolyl, or pyridyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy,
    vii) $C_{1-8}$ alkylthio,
    viii) $C_{1-8}$ alkylsulfonyl,
    ix) sulfamoyl, or
    x) $C_{1-8}$ alkyl;
  c) $C_{3-8}$ cycloalkyl,
  d) $C_{1-8}$ alkylthio,
  e) $C_{1-8}$ alkylsulfonyl,
  f) $C_{1-8}$ alkoxy, or
  g) aryl $C_{1-8}$ alkyl sulfonyl;

$R^3$ is: $C_{0-4}$ alkyl, which is substituted with a substituent selected from the group consisting of:
  a) unsubstituted or substituted aryl, which is as defined in $R^2$(a), b) unsubstituted or substituted heteroaryl, which is as defined in R²(b); and R⁴ is: H.

3. The tetrapeptide as recited in claim 1 represented by Formula I:

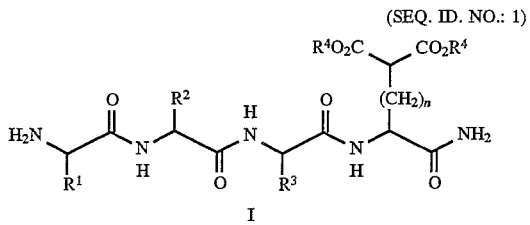

(SEQ. ID. NO.: 1)

I or the pharmaceutically acceptable salts, hydrates, esters or amides thereof, wherein:

n is: 0 to 4;

R¹ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

R² is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide;

R³ is: $C_{0-4}$ alkyl, which is substituted with a substituent selected from the group consisting of:

a) aryl, which is defined as phenyl or naphthyl, unsubstituted or substituted with one, two, three or four substituents selected from the group consisting of:
  i) F,
  ii) Cl,
  iii) Br,
  iv) nitro,
  v) cyano,
  vi) $C_{1-8}$ alkoxy,
  vii) $C_{1-8}$ alkylthio,
  viii) $C_{1-8}$ alkylsulfonyl,
  ix) sulfamoyl, or
  x) $C_{1-8}$ alkyl; or b) heteroaryl, which is defined as indolyl, imidazolyl or pyridyl, unsubstituted or substituted with one, two, three or four substituents selected from the group consisting of:
  i) F,
  ii) Cl,
  iii) Br,
  iv) nitro,
  v) cyano,
  vi) $C_{1-8}$ alkoxy,
  vii) $C_{1-8}$ alkylthio,
  viii) $C_{1-8}$ alkylsulfonyl,
  ix) sulfamoyl, or
  x) $C_{1-8}$ alkyl; and R⁴ is: H.

4. The tetrapeptide of claim 1 represented by Formula I:

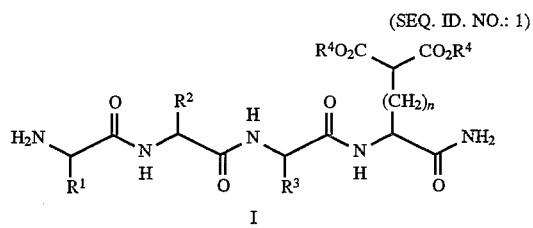

(SEQ. ID. NO.: 1)

I or the pharmaceutically acceptable salts, hydrates, esters or amides thereof, wherein:

n is: 0 to 4;

R¹ and R³ independently are: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

R² is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide; and R⁴ is: H.

5. The tetrapeptide of claim 1 represented by Formula I:

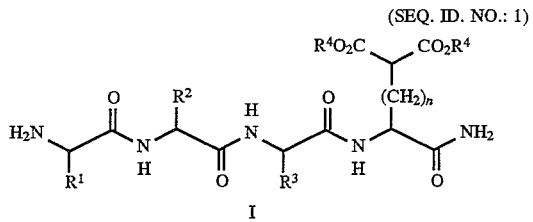

(SEQ. ID. NO.: 1)

I wherein:

n is: 0 to 4;

R¹ is: 3-indolylmethyl;

R² is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide;

R³ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl; and R⁴ is: H.

6. The tetrapeptide of claim 5 represented by Formula I:

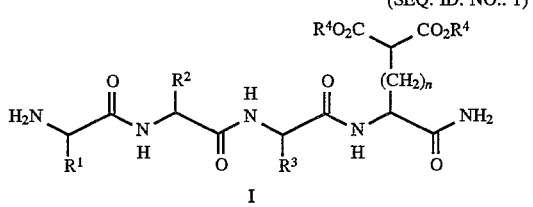

(SEQ. ID. NO.: 1)

I wherein:

n is: 0 to 4;

R¹ is: 3-indolylmethyl;

R² is: 3-indolylmethyl, benzyl, or 3-thiabutyl;

R³ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl; and R⁴ is: H.

7. The tetrapeptide of claim 6 represented by Formula I:

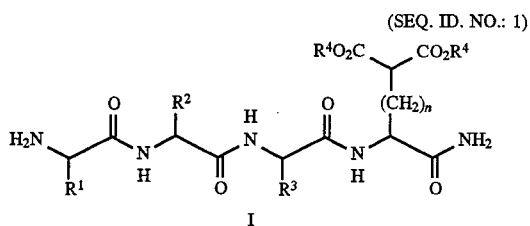

(SEQ. ID. NO.: 1)

I wherein:

n is: 0 to 4;

$R^1$ is: 3-indolylmethyl;

$R^2$ is: 3-indolylmethyl, benzyl, or 3-thiabutyl;

$R^3$ is: 3-indolylmethyl, 4-chlorobenzyl, or benzyl; and $R^4$ is: H.

8. The tetrapeptide of claim 7 represented by Formula I:

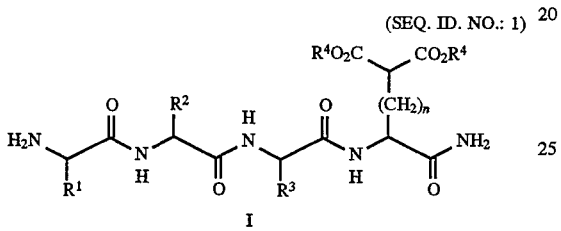

(SEQ. ID. NO.: 1)

I wherein:

n is: 1;

$R^1$ is: 3-indolylmethyl;

$R^2$ is: 3-indolylmethyl, benzyl, or 3-thiabutyl;

$R^3$ is: 3-indolylmethyl, 4-chlorobenzyl, or benzyl; and $R^4$ is: H.

9. The tetrapeptide as recited in claim 8 selected from the group consisting of:

D-Tryptophyl-D-phenylalanyl-D-phenylalanyl-L-γ-carboxyglutamyl amide; (SEQ.ID.NO.: 2)

D-Tryptophyl-D-phenylalanyl-D-tryptophyl-L-γ-carboxyglutamyl amide; (SEQ.ID.NO.: 3)

D-Tryptophyl-D-phenylalanyl-D-p-chlorophenylalanyl-L-γ-carboxyglutamyl amide; (SEQ.ID.NO.: 4)

D-Tryptophyl-D-phenylalanyl-L-p-chlorophenylalanyl-L-γ-carboxyglutamyl amide; (SEQ.ID.NO.: 5)

D-Tryptophyl-D-tryptophyl-D-phenylalanyl-L-γ-carboxyglutamyl amide; (SEQ.ID.NO.: 6)

D-Tryptophyl-D-tryptophyl-D-tryptophyl-L-γ-carboxyglutamyl amide; (SEQ.ID.NO.: 7)

D-Tryptophyl-D-tryptophyl-D-p-chlorophenylalanyl-L-γ-carboxyglutamyl amide; (SEQ.ID.NO.: 8)

D-Tryptophyl-D-tryptophyl-L-p-chlorophenylalanyl-L-γ-carboxyglutamyl amide; (SEQ.ID.NO.: 9)

D-Tryptophyl-D-methioninyl-D-phenylalanyl-L-γ-carboxyglutamyl amide; (SEQ.ID.NO.: 10)

D-Tryptophyl-D-methioninyl-D-tryptophyl-L-γ-carboxyglutamyl amide; (SEQ.ID.NO.: 11)

D-Tryptophyl-D-methioninyl-D-p-chlorophenylalanyl-L-γ-carboxyglutamyl amide; (SEQ.ID.NO.: 12)

D-Tryptophyl-D-methioninyl-L-p-chlorophenylalanyl-L-γ-carboxyglutamyl amide; (SEQ.ID.NO.: 13)

D-Tryptophyl-L-tryptophyl-D-phenylalanyl-L-γ-carboxyglutamyl amide; (SEQ.ID.NO.: 14)

D-Tryptophyl-L-tryptophyl-D-tryptophyl-L-γ-carboxyglutamyl amide; (SEQ.ID.NO.: 15)

D-Tryptophyl-L-tryptophyl-D-p-chlorophenylalanyl-L-γ-carboxyglutamyl amide; and (SEQ.ID.NO.: 16)

D-Tryptophyl-L-tryptophyl-L-p-chlorophenylalanyl-L-γ-carboxyglutamyl amide (SEQ.ID.NO.: 17).

10. A tetrapeptide which is:

D-Tryptophyl-D-phenylalanyl-D-p-chlorophenylalanyl-L-γ-carboxyglutamyl amide (SEQ.ID.NO.: 4).

11. A tetrapeptide which is:

D-Tryptophyl-D-tryptophyl-D-p-chlorophenylalanyl-L-γ-carboxyglutamyl amide (SEQ.ID.NO.: 8).

12. A tetrapeptide which is:

D-Tryptophyl-D-methioninyl-D-phenylalanyl-L-γ-carboxyglutamyl amide (SEQ.ID.NO.: 10).

13. A tetrapeptide which is:

D-Tryptophyl-D-methioninyl-D-p-chlorophenylalanyl-L-γ-carboxyglutamyl amide (SEQ.ID.NO.: 12).

14. A tetrapeptide represented by Formula I:

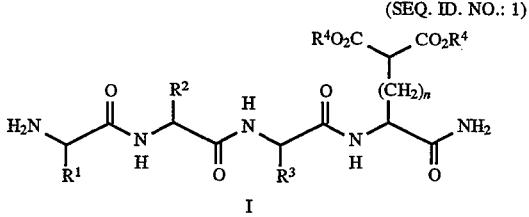

(SEQ. ID. NO.: 1)

I or the pharmaceutically acceptable salts, hydrates, esters or amides thereof, wherein:

n is: 0 to 4, $R^1$ and $R^3$ independently are $C_{0-4}$ alkyl, substituted with substituents selected from the group consisting of:

a) aryl, which is defined as phenyl or naphthyl, unsubstituted or substituted with one, two, three or four substituents selected from the group consisting of:

i) F, ii) Cl, iii) Br, iv) nitro, v) cyano, vi) $C_{1-8}$ alkoxy, vii) $C_{1-8}$ alkylthio, viii) $C_{1-8}$ alkylsulfonyl, ix) sulfamoyl, or x) $C_{1-8}$ alkyl; or b) heteroaryl, which is defined as indolyl, imidazolyl or pyridyl, unsubstituted or substituted with one, two, three or four substituents selected from the group consisting of:

i) F, ii) Cl, iii) Br, iv) nitro, v) cyano, vi) $C_{1-8}$ alkoxy, vii) $C_{1-8}$ alkylthio, viii) $C_{1-8}$ alkylsulfonyl, ix) sulfamoyl, or x) $C_{1-8}$ alkyl;

$R^2$ is: $C_{0-6}$ alkyl, which is unsubstituted or substituted with a substituent selected from the group consisting of:

a) unsubstituted or substituted aryl, as defined in $R^1$(a), b) unsubstituted or substituted heteroaryl, as defined in $R^1$(b), c) $C_{3-8}$ cycloalkyl, d) $C_{1-8}$ alkylthio,
e) $C_{1-8}$ alkylsulfonyl,
f) $C_{1-8}$ alkoxy, or
g) aryl $C_{1-8}$ alkyl sulfonyl; and $R^4$ is:
a) $C_{1-6}$ alkyl,
b) aryl, which is as defined in $R^1$(a),
c) $C_{1-6}$ alkylaryl, where aryl is as defined in $R^1$(a), or
d)

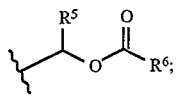

$R^5$ is: H or $C_{1-6}$ alkyl; and
$R^6$ is: $C_{1-6}$ alkyl.

15. The tetrapeptide as recited in claim 14 represented by Formula I:

(SEQ. ID. NO.: 1)

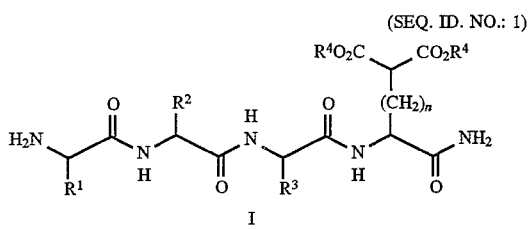

I or the pharmaceutically acceptable salts, hydrates, esters or amides thereof, wherein:

n is: 0 to 4;
$R^1$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl;
$R^2$ is: $C_{0-6}$ alkyl, which is unsubstituted or substituted with a substituent selected from the group consisting of:
  a) aryl, which is defined as phenyl or naphthyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy,
    vii) $C_{1-8}$ alkylthio,
    viii) $C_{1-8}$ alkylsulfonyl,
    ix) sulfamoyl, or
    x) $C_{1-8}$ alkyl;
  b) heteroaryl, which is defined as indolyl, imidazolyl, or pyridyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy,
    vii) $C_{1-8}$ alkylthio,
    viii) $C_{1-8}$ alkylsulfonyl,
    ix) sulfamoyl, or
    x) $C_{1-8}$ alkyl;
  c) $C_{3-8}$ cycloalkyl,
  d) $C_{1-8}$ alkylthio,
  e) $C_{1-8}$ alkylsulfonyl,
  f) $C_{1-8}$ alkoxy, or
  g) aryl $C_{1-8}$ alkyl sulfonyl;

$R^3$ is: $C_{0-4}$ alkyl, which is substituted with a substituent selected from the group consisting of:
  a) unsubstituted or substituted aryl, which is as defined in $R^2$(a),
  b) unsubstituted or substituted heteroaryl, which is as defined in $R^2$(b); and $R^4$ is:
a) $C_{1-6}$ alkyl,
b) aryl, which is as defined in $R^2$(a),
c) $C_{1-6}$ alkylaryl, where aryl is as defined in $R^2$(a), or
d)

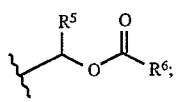

$R^5$ is: H or $C_{1-6}$ alkyl; and
$R^6$ is: $C_{1-6}$ alkyl.

16. The tetrapeptide as recited in claim 14 represented by Formula I:

(SEQ. ID. NO.: 1)

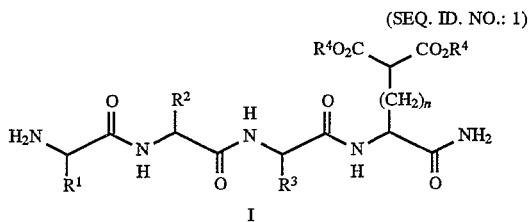

I or the pharmaceutically acceptable salts, hydrates, esters or amides thereof, wherein:

n is: 0 to 4;
$R^1$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl;
$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide;
$R^3$ is: $C_{0-4}$ alkyl, which is substituted with a substituent selected from the group consisting of:
  a) aryl, which is defined as phenyl or naphthyl, unsubstituted or substituted with one, two, three or four substituents selected from the group consisting of:
    i) F,
    ii) Cl,
    iii) Br,
    iv) nitro,
    v) cyano,
    vi) $C_{1-8}$ alkoxy,
    vii) $C_{1-8}$ alkylthio,
    viii) $C_{1-8}$ alkylsulfonyl,
    ix) sulfamoyl, or
    x) $C_{1-8}$ alkyl; or
  b) heteroaryl, which is defined as indolyl, imidazolyl or pyridyl, unsubstituted or substituted with one, two, three or four substituents selected from the group consisting of:
    i) F,
    ii) Cl, iii) Br,
iv) nitro,
v) cyano,
vi) $C_{1-8}$ alkoxy,
vii) $C_{1-8}$ alkylthio,
viii) $C_{1-8}$ alkylsulfonyl,
ix) sulfamoyl, or
x) $C_{1-8}$ alkyl; and $R^4$ is:
a) $C_{1-6}$ alkyl,
b) aryl, which is as defined in $R^3$(a),
c) $C_{1-6}$ alkylaryl, where aryl is as defined in $R^3$(a), or
d)

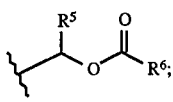

$R^5$ is: H or $C_{1-6}$ alkyl; and
$R^6$ is: $C_{1-6}$ alkyl.

17. The tetrapeptide of claim 14 represented by Formula I:

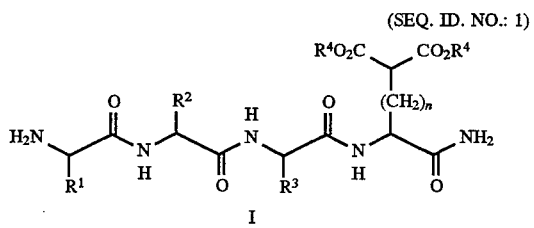

(SEQ. ID. NO.: 1)

or the pharmaceutically acceptable salts, hydrates, esters or amides thereof, wherein:

n is: 0 to 4;

$R^1$ and $R^3$ independently are: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide; and $R^4$ is:
a) $C_{1-6}$ alkyl,
b) aryl, which is as defined in $R^1$(a),
c) $C_{1-6}$ alkylaryl, where aryl is as defined in $R^1$(a), or
d)

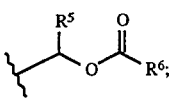

$R^5$ is: H or $C_{1-6}$ alkyl; and
$R^6$ is: $C_{1-6}$ alkyl.

18. The tetrapeptide of claim 14 represented by Formula I:

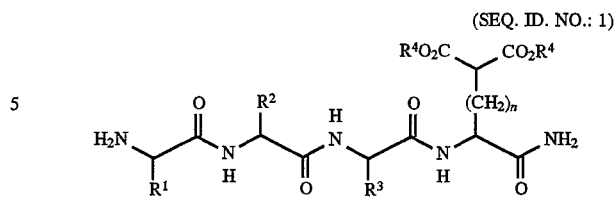

(SEQ. ID. NO.: 1)

wherein:

n is: 0 to 4;

$R^1$ and $R^3$ independently are: 3-indolylmethyl, benzyl, 4-chlorobenzyl, 4-methoxybenzyl, 4-nitrobenzyl, 4-hydroxybenzyl, 4-fluorobenzyl, or 2-phenylethyl;

$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide; and $R^4$ is: $C_{1-6}$ alkyl, or

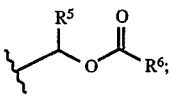

$R^5$ is: H or $C_{1-6}$ alkyl; and
$R^6$ is: $C_{1-6}$ alkyl.

19. The tetrapeptide of claim 18 represented by Formula I:

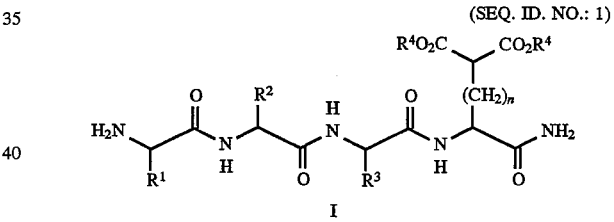

(SEQ. ID. NO.: 1)

wherein:

n is: 0 to 4;

$R^1$ is: 3-indolylmethyl;

$R^2$ is: 3-indolylmethyl, 4-imidazolylmethyl, 2(S)-butyl, 2-methylpropyl, 3-thiabutyl, benzyl, 4-hydroxybenzyl, 4-fluorobenzyl, isopropyl, 4-cyclohexylmethyl, 4-nitrobenzyl, 3-pyridylmethyl, butyl, 4-chlorobenzyl, phenyl or 3-thiabutyl-S,S-dioxide;

$R^3$ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl; and $R^4$ is: $C_{1-6}$ alkyl, or

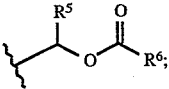

$R^5$ is: H or $C_{1-6}$ alkyl; and
$R^6$ is: $C_{1-6}$ alkyl.

20. The tetrapeptide of claim 19 represented by Formula I:

(SEQ. ID. NO.: 1)

[Structure I: tetrapeptide with H2N-CHR¹-CO-NH-CHR²-CO-NH-CHR³-CO-NH-CH((CH2)n-C(CO2R⁴)(CO2R⁴)H)-CO-NH2]

I wherein:
n is: 0 to 4;
R¹ is: 3-indolylmethyl;
R² is: 3-indolylmethyl, benzyl, or 3-thiabutyl;
R³ is: 3-indolylmethyl, benzyl, 4-chlorobenzyl, 4-methoxybenzyl, 4-nitrobenzyl, 4-hydroxybenzyl, 4-fluorobenzyl, or 2-phenylethyl; and
R⁴ is: $C_{1-6}$ alkyl, or

[Structure: -CH(R⁵)-O-C(=O)-R⁶]

R⁵ is: H or $C_{1-6}$ alkyl; and
R⁶ is: $C_{1-6}$ alkyl.

21. The tetrapeptide of claim 20 represented by Formula I:

(SEQ. ID. NO.: 1)

[Structure I]

I wherein:
n is: 0 to 4;
R¹ is: 3-indolylmethyl;
R² is: 3-indolylmethyl, benzyl, or 3-thiabutyl;
R³ is: 3-indolylmethyl, 4-chlorobenzyl, or benzyl; and
R⁴ is: $C_{1-6}$ alkyl, or

[Structure: -CH(R⁵)-O-C(=O)-R⁶]

R⁵ is: H or $C_{1-6}$ alkyl; and
R⁶ is: $C_{1-6}$ alkyl.

22. The tetrapeptide of claim 21 represented by Formula I:

(SEQ. ID. NO.: 1)

[Structure I]

I wherein:
n is: 1;
R¹ is: 3-indolylmethyl;
R² is: 3-indolylmethyl, benzyl, or 3-thiabutyl;
R³ is: 3-indolylmethyl, 4-chlorobenzyl, or benzyl;
R⁴ is: methyl, ethyl, isopropyl, isobutyl or

[Structure: -CH(R⁵)-O-C(=O)-R⁶]

R⁵ is: H or methyl; and
R⁶ is: 1,1-dimethylethyl.

23. The tetrapeptide as recited in claim 22 selected from the group consisting of:
D-Tryptophyl-D-phenylalanyl-D-phenylalanyl-L-γ-carboxyglutamyl amide dimethyl ester; (SEQ.ID.NO.: 18)
D-Tryptophyl-D-phenylalanyl-D-tryptophyl-L-γ-carboxyglutamyl amide dimethyl ester; (SEQ.ID.NO.: 19)
D-Tryptophyl-D-phenylalanyl-D-p-chlorophenylalanyl-L-γ-carboxyglutamyl amide dimethyl ester; (SEQ.ID.NO.: 20)
D-Tryptophyl-D-phenylalanyl-L-p-chlorophenylalanyl-L-γ-carboxyglutamyl amide dimethyl ester; (SEQ.ID.NO.: 21)
D-Tryptophyl-D-tryptophyl-D-phenylalanyl-L-γ-carboxyglutamyl amide dimethyl ester; (SEQ.ID.NO.: 22)
D-Tryptophyl-D-tryptophyl-D-tryptophyl-L-γ-carboxyglutamyl amide dimethyl ester; (SEQ.ID.NO.: 23)
D-Tryptophyl-D-tryptophyl-D-p-chlorophenylalanyl-L-γ-carboxyglutamyl amide dimethyl ester; (SEQ.ID.NO.: 24)
D-Tryptophyl-D-tryptophyl-L-p-chlorophenylalanyl-L-γ-carboxyglutamyl amide dimethyl ester; (SEQ.ID.NO.: 25)
D-Tryptophyl-D-methioninyl-D-phenylalanyl-L-γ-carboxyglutamyl amide dimethyl ester; (SEQ.ID.NO.: 26)
D-Tryptophyl-D-methioninyl-D-tryptophyl-L-γ-carboxyglutamyl amide dimethyl ester; (SEQ.ID.NO.: 27)
D-Tryptophyl-D-methioninyl-D-p-chlorophenylalanyl-L-γ-carboxyglutamyl amide dimethyl ester; (SEQ.ID.NO.: 28)
D-Tryptophyl-D-methioninyl-L-p-chlorophenylalanyl-L-γ-carboxyglutamyl amide dimethyl ester; (SEQ.ID.NO.: 29)
D-Tryptophyl-L-tryptophyl-D-phenylalanyl-L-γ-carboxyglutamyl amide dimethyl ester; (SEQ.ID.NO.: 30)
D-Tryptophyl-L-tryptophyl-D-tryptophyl-L-γ-carboxyglutamyl amide dimethyl ester; (SEQ.ID.NO.: 31)
D-Tryptophyl-L-tryptophyl-D-p-chlorophenylalanyl-L-γ-carboxyglutamyl amide dimethyl ester; and (SEQ.ID.NO.: 32)
D-Tryptophyl-L-tryptophyl-L-p-chlorophenylalanyl-L-γ-carboxyglutamyl amide dimethyl ester (SEQ.ID.NO.: 33).

24. The tetrapeptide as recited in claim 14 which is:
D-Tryptophyl-D-phenylalanyl-D-p-chlorophenylalanyl-L-γ-carboxyglutamyl amide dimethyl ester (SEQ.ID.NO.: 20).

25. The tetrapeptide as recited in claim 14 which is:

D-Tryptophyl-D-tryptophyl-D-p-chlorophenylalanyl-L-γ-carboxyglutamyl amide dimethyl ester (SEQ.ID.NO.: 24).

26. A tetrapeptide as recited in claim 14 which is:

D-Tryptophyl-D-methioninyl-D-phenylalanyl-L-γ-carboxyglutamyl amide dimethyl ester (SEQ.ID.NO.: 26).

27. The tetrapeptide as recited in claim 14 which is:

D-Tryptophyl-D-methioninyl-D-p-chlorophenylalanyl-L-γ-carboxyglutamyl amide dimethyl ester (SEQ.ID.NO.: 28).

28. A pharmaceutical composition comprising a pharmaceutically acceptable carrier and dispersed therein, a therapeutically effective amount of a tetrapeptide of Formula I as recited in claim 1.

29. A pharmaceutical composition comprising a pharmaceutically acceptable carrier and dispersed therein, a therapeutically effective amount of a tetrapeptide of Formula I as recited in claim 14.

30. A method of inhibiting cancer in a mammal, the treatment of which is effected or facilitated by the inhibition of farnesyl protein transferase, comprising the administration of a tetrapeptide of Formula I as recited in claim 1, in an amount that is therapeutically effective for inhibiting farnesyl-protein transferase.

31. A method of inhibiting cancer in a mammal, the treatment of which is effected or facilitated by the inhibition of farnesyl protein transferase, comprising the administration of a tetrapeptide of Formula I as recited in claim 14, in an amount that is therapeutically effective for inhibiting farnesyl-protein transferase.

32. The method of inhibiting cancer in a mammal as recited in claim 28, which is effected or facilitated by the inhibition of farnesylation of the Ras protein.

33. The method of inhibiting cancer in a mammal as recited in claim 29, which is effected or facilitated by the inhibition of farnesylation of the Ras protein.

34. A method for treating cancer which comprises administering to a mammal in need thereof a therapeutically effective amount of a tetrapeptide of Formula I as recited in claim 1.

35. A method for treating cancer which comprises administering to a mammal in need thereof a therapeutically effective amount of a tetrapeptide of Formula I as recited in claim 14.

36. A method for inhibiting farnesyl-protein transferase which comprises administering to a mammal in need thereof a therapeutically effective amount of a tetrapeptide of Formula I as recited in claim 1.

37. A method for inhibiting farnesyl-protein transferase which comprises administering to a mammal in need thereof a therapeutically effective amount of a tetrapeptide of Formula I as recited in claim 14.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Xaa Xaa Xaa Xaa
1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="D-Tryptophyl"

( i x ) FEATURE:
    ( A ) NAME/KEY: Peptide
    ( B ) LOCATION: 2
    ( D ) OTHER INFORMATION: /product="D-phenylalanyl"

( i x ) FEATURE:
    ( A ) NAME/KEY: Peptide
    ( B ) LOCATION: 3
    ( D ) OTHER INFORMATION: /product="D-phenylalanyl"

( i x ) FEATURE:
    ( A ) NAME/KEY: Peptide
    ( B ) LOCATION: 4
    ( D ) OTHER INFORMATION: /product="L-4-carboxylglutamyl amide"

( x i ) SEQUENCE DESCRIPTION: SEQ ID NO:2:

Xaa Xaa Xaa Xaa
1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="D-Tryptophyl"

( i x ) FEATURE:
        ( A ) NAME/KEY: Peptide
        ( B ) LOCATION: 2
        ( D ) OTHER INFORMATION: /product="D-phenylalanyl"

( i x ) FEATURE:
        ( A ) NAME/KEY: Peptide
        ( B ) LOCATION: 3
        ( D ) OTHER INFORMATION: /product="D-tryptophyl"

( i x ) FEATURE:
        ( A ) NAME/KEY: Peptide
        ( B ) LOCATION: 4
        ( D ) OTHER INFORMATION: /product="L-4-carboxyglutamyl amide"

( x i ) SEQUENCE DESCRIPTION: SEQ ID NO:3:

Xaa Xaa Xaa Xaa
1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="D-Tryptophyl"

( i x ) FEATURE:
        ( A ) NAME/KEY: Peptide
        ( B ) LOCATION: 2
        ( D ) OTHER INFORMATION: /product="D-phenylalanyl"

( i x ) FEATURE:
    ( A ) NAME/KEY: Peptide
    ( B ) LOCATION: 3
    ( D ) OTHER INFORMATION: /product="D-p-chlorophenylalanyl"

( i x ) FEATURE:
    ( A ) NAME/KEY: Peptide
    ( B ) LOCATION: 4
    ( D ) OTHER INFORMATION: /product="L-4-carboxyglutamyl amide"

( x i ) SEQUENCE DESCRIPTION: SEQ ID NO:4:

Xaa Xaa Xaa Xaa
1

( 2 ) INFORMATION FOR SEQ ID NO:5:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-Tryptophyl"

( i x ) FEATURE:
    ( A ) NAME/KEY: Peptide
    ( B ) LOCATION: 2
    ( D ) OTHER INFORMATION: /product="D-phenylalanyl"

( i x ) FEATURE:
    ( A ) NAME/KEY: Peptide
    ( B ) LOCATION: 3
    ( D ) OTHER INFORMATION: /product="L-p-chlorophenylalanyl"

( i x ) FEATURE:
    ( A ) NAME/KEY: Peptide
    ( B ) LOCATION: 4
    ( D ) OTHER INFORMATION: /product="L-4-carboxyglutamyl amide"

( x i ) SEQUENCE DESCRIPTION: SEQ ID NO:5:

Xaa Xaa Xaa Xaa
1

( 2 ) INFORMATION FOR SEQ ID NO:6:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-Tryptophyl"

( i x ) FEATURE:
    ( A ) NAME/KEY: Peptide
    ( B ) LOCATION: 2
    ( D ) OTHER INFORMATION: /product="D-tryptophyl"

( i x ) FEATURE:
    ( A ) NAME/KEY: Peptide
    ( B ) LOCATION: 3
    ( D ) OTHER INFORMATION: /product="D-phenylalanyl"

( i x ) FEATURE:

(A) NAME/KEY: Peptide
(B) LOCATION: 4
(D) OTHER INFORMATION: /product="L-4-carboxyglutamyl amide"

(xi) SEQUENCE DESCRIPTION: SEQ ID NO:6:

Xaa Xaa Xaa Xaa
1

(2) INFORMATION FOR SEQ ID NO:7:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1
(D) OTHER INFORMATION: /product="D-tryptophyl"

(ix) FEATURE:
(A) NAME/KEY: Peptide
(B) LOCATION: 2
(D) OTHER INFORMATION: /product="D-tryptophyl"

(ix) FEATURE:
(A) NAME/KEY: Peptide
(B) LOCATION: 3
(D) OTHER INFORMATION: /product="D-tryptophyl"

(ix) FEATURE:
(A) NAME/KEY: Peptide
(B) LOCATION: 4
(D) OTHER INFORMATION: /product="L-4-carboxyglutamyl amide"

(xi) SEQUENCE DESCRIPTION: SEQ ID NO:7:

Xaa Xaa Xaa Xaa
1

(2) INFORMATION FOR SEQ ID NO:8:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1
(D) OTHER INFORMATION: /product="D-tryptophyl"

(ix) FEATURE:
(A) NAME/KEY: Peptide
(B) LOCATION: 2
(D) OTHER INFORMATION: /product="D-tryptophyl"

(ix) FEATURE:
(A) NAME/KEY: Peptide
(B) LOCATION: 3
(D) OTHER INFORMATION: /product="D-p-chlorophenylalanyl"

(ix) FEATURE:
(A) NAME/KEY: Peptide
(B) LOCATION: 4
(D) OTHER INFORMATION: /product="L-4-carboxyglutamyl amide"

(xi) SEQUENCE DESCRIPTION: SEQ ID NO:8:

```
Xaa Xaa Xaa Xaa
1
```

(2) INFORMATION FOR SEQ ID NO:9:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /product="D-tryptophyl"

(ix) FEATURE:
        (A) NAME/KEY: Peptide
        (B) LOCATION: 2
        (D) OTHER INFORMATION: /product="D-tryptophyl"

(ix) FEATURE:
        (A) NAME/KEY: Peptide
        (B) LOCATION: 3
        (D) OTHER INFORMATION: /product="L-p-chlorophenylalanyl"

(ix) FEATURE:
        (A) NAME/KEY: Peptide
        (B) LOCATION: 4
        (D) OTHER INFORMATION: /product="L-4-carboxyglutamyl amide"

(xi) SEQUENCE DESCRIPTION: SEQ ID NO:9:

```
Xaa Xaa Xaa Xaa
1
```

(2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /product="D-tryptophyl"

(ix) FEATURE:
        (A) NAME/KEY: Peptide
        (B) LOCATION: 2
        (D) OTHER INFORMATION: /product="D-methioninyl"

(ix) FEATURE:
        (A) NAME/KEY: Peptide
        (B) LOCATION: 3
        (D) OTHER INFORMATION: /product="D-phenylalanyl"

(ix) FEATURE:
        (A) NAME/KEY: Peptide
        (B) LOCATION: 4
        (D) OTHER INFORMATION: /product="L-4-carboxyglutamyl amide"

(xi) SEQUENCE DESCRIPTION: SEQ ID NO:10:

```
Xaa Xaa Xaa Xaa
1
```

(2) INFORMATION FOR SEQ ID NO:11:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-tryptophyl"

( i x ) FEATURE:
    ( A ) NAME/KEY: Peptide
    ( B ) LOCATION: 2
    ( D ) OTHER INFORMATION: /product="D-methioninyl"

( i x ) FEATURE:
    ( A ) NAME/KEY: Peptide
    ( B ) LOCATION: 3
    ( D ) OTHER INFORMATION: /product="D-tryptophyl"

( i x ) FEATURE:
    ( A ) NAME/KEY: Peptide
    ( B ) LOCATION: 4
    ( D ) OTHER INFORMATION: /product="L-4-carboxyglutamyl
        amide"

( x i ) SEQUENCE DESCRIPTION: SEQ ID NO:11:

Xaa Xaa Xaa Xaa
1

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="D-tryptophyl"

( i x ) FEATURE:
        ( A ) NAME/KEY: Peptide
        ( B ) LOCATION: 2
        ( D ) OTHER INFORMATION: /product="D-methioninyl"

( i x ) FEATURE:
        ( A ) NAME/KEY: Peptide
        ( B ) LOCATION: 3
        ( D ) OTHER INFORMATION: /product="D-p-chlorophenylalanyl"

( i x ) FEATURE:
        ( A ) NAME/KEY: Peptide
        ( B ) LOCATION: 4
        ( D ) OTHER INFORMATION: /product="L-4-carboxyglutamyl
            amide"

( x i ) SEQUENCE DESCRIPTION: SEQ ID NO:12:

Xaa Xaa Xaa Xaa
1

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-tryptophyl"

( i x ) FEATURE:
    ( A ) NAME/KEY: Peptide
    ( B ) LOCATION: 2
    ( D ) OTHER INFORMATION: /product="D-methioninyl"

( i x ) FEATURE:
    ( A ) NAME/KEY: Peptide
    ( B ) LOCATION: 3
    ( D ) OTHER INFORMATION: /product="L-p-chlorophenylalanyl"

( i x ) FEATURE:
    ( A ) NAME/KEY: Peptide
    ( B ) LOCATION: 4
    ( D ) OTHER INFORMATION: /product="L-4-carboxyglutamyl
        amide"

( x i ) SEQUENCE DESCRIPTION: SEQ ID NO:13:

Xaa Xaa Xaa Xaa
1

( 2 ) INFORMATION FOR SEQ ID NO:14:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-tryptophyl"

( i x ) FEATURE:
    ( A ) NAME/KEY: Peptide
    ( B ) LOCATION: 3
    ( D ) OTHER INFORMATION: /product="D-phenylalanyl"

( i x ) FEATURE:
    ( A ) NAME/KEY: Peptide
    ( B ) LOCATION: 4
    ( D ) OTHER INFORMATION: /product="L-4-carboxyglutamyl
        amide"

( x i ) SEQUENCE DESCRIPTION: SEQ ID NO:14:

Xaa Trp Xaa Xaa
1

( 2 ) INFORMATION FOR SEQ ID NO:15:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-tryptophyl"

( i x ) FEATURE:
    ( A ) NAME/KEY: Peptide
    ( B ) LOCATION: 3

( D ) OTHER INFORMATION: /product="D-tryptophyl"

( i x ) FEATURE:
    ( A ) NAME/KEY: Peptide
    ( B ) LOCATION: 4
    ( D ) OTHER INFORMATION: /product="L-4-carboxyglutamyl
        amide"

( x i ) SEQUENCE DESCRIPTION: SEQ ID NO:15:

Xaa Trp Xaa Xaa
1

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="D-tryptophyl"

( i x ) FEATURE:
        ( A ) NAME/KEY: Peptide
        ( B ) LOCATION: 3
        ( D ) OTHER INFORMATION: /product="D-p-chlorophenylalanyl"

( i x ) FEATURE:
        ( A ) NAME/KEY: Peptide
        ( B ) LOCATION: 4
        ( D ) OTHER INFORMATION: /product="L-4-carboxyglutamyl
            amide"

( x i ) SEQUENCE DESCRIPTION: SEQ ID NO:16:

Xaa Trp Xaa Xaa
1

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="D-tryptophyl"

( i x ) FEATURE:
        ( A ) NAME/KEY: Peptide
        ( B ) LOCATION: 3
        ( D ) OTHER INFORMATION: /product="L-p-chlorophenylalanyl"

( i x ) FEATURE:
        ( A ) NAME/KEY: Peptide
        ( B ) LOCATION: 4
        ( D ) OTHER INFORMATION: /product="L-4-carboxyglutamyl
            amide"

( x i ) SEQUENCE DESCRIPTION: SEQ ID NO:17:

Xaa Trp Xaa Xaa
1

( 2 ) INFORMATION FOR SEQ ID NO:18:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1
  ( D ) OTHER INFORMATION: /product="D-tryptophyl"

( i x ) FEATURE:
  ( A ) NAME/KEY: Peptide
  ( B ) LOCATION: 2
  ( D ) OTHER INFORMATION: /product="D-phenylalanyl"

( i x ) FEATURE:
  ( A ) NAME/KEY: Peptide
  ( B ) LOCATION: 3
  ( D ) OTHER INFORMATION: /product="D-phenylalanyl"

( i x ) FEATURE:
  ( A ) NAME/KEY: Peptide
  ( B ) LOCATION: 4
  ( D ) OTHER INFORMATION: /product="L-4-carboxyglutamyl
    amide dimethyl ester"

( x i ) SEQUENCE DESCRIPTION: SEQ ID NO:18:

Xaa Xaa Xaa Xaa
1

( 2 ) INFORMATION FOR SEQ ID NO:19:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-tryptophyl"

( i x ) FEATURE:
    ( A ) NAME/KEY: Peptide
    ( B ) LOCATION: 2
    ( D ) OTHER INFORMATION: /product="D-phenylalanyl"

( i x ) FEATURE:
    ( A ) NAME/KEY: Peptide
    ( B ) LOCATION: 3
    ( D ) OTHER INFORMATION: /product="D-tryptophyl"

( i x ) FEATURE:
    ( A ) NAME/KEY: Peptide
    ( B ) LOCATION: 4
    ( D ) OTHER INFORMATION: /product="L-4-carboxyglutamyl
      amide dimethyl ester"

( x i ) SEQUENCE DESCRIPTION: SEQ ID NO:19:

Xaa Xaa Xaa Xaa
1

( 2 ) INFORMATION FOR SEQ ID NO:20:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-tryptophyl"

( i x ) FEATURE:
    ( A ) NAME/KEY: Peptide
    ( B ) LOCATION: 2
    ( D ) OTHER INFORMATION: /product="D-phenylalanyl"

( i x ) FEATURE:
    ( A ) NAME/KEY: Peptide
    ( B ) LOCATION: 3
    ( D ) OTHER INFORMATION: /product="D-p-chlorophenylalanyl"

( i x ) FEATURE:
    ( A ) NAME/KEY: Peptide
    ( B ) LOCATION: 4
    ( D ) OTHER INFORMATION: /product="L-4-carboxyglutamyl
        amide dimethyl ester"

( x i ) SEQUENCE DESCRIPTION: SEQ ID NO:20:

Xaa Xaa Xaa Xaa
1

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="D-tryptophyl"

( i x ) FEATURE:
        ( A ) NAME/KEY: Peptide
        ( B ) LOCATION: 2
        ( D ) OTHER INFORMATION: /product="D-phenylalanyl"

( i x ) FEATURE:
        ( A ) NAME/KEY: Peptide
        ( B ) LOCATION: 3
        ( D ) OTHER INFORMATION: /product="L-p-chlorophenylalanyl"

( i x ) FEATURE:
        ( A ) NAME/KEY: Peptide
        ( B ) LOCATION: 4
        ( D ) OTHER INFORMATION: /product="L-4-carboxyglutamyl
            amide dimethyl ester"

( x i ) SEQUENCE DESCRIPTION: SEQ ID NO:21:

Xaa Xaa Xaa Xaa
1

( 2 ) INFORMATION FOR SEQ ID NO:22:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /product="D-tryptophyl"

( i x ) FEATURE:
    ( A ) NAME/KEY: Peptide
    ( B ) LOCATION: 2
    ( D ) OTHER INFORMATION: /product="D-tryptophyl"

( i x ) FEATURE:
    ( A ) NAME/KEY: Peptide
    ( B ) LOCATION: 3
    ( D ) OTHER INFORMATION: /product="D-phenylalanyl"

( i x ) FEATURE:
    ( A ) NAME/KEY: Peptide
    ( B ) LOCATION: 4
    ( D ) OTHER INFORMATION: /product="L-4-carboxyglutamyl amide dimethyl ester"

( x i ) SEQUENCE DESCRIPTION: SEQ ID NO:22:

Xaa Xaa Xaa Xaa
1

( 2 ) INFORMATION FOR SEQ ID NO:23:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-tryptophyl"

( i x ) FEATURE:
    ( A ) NAME/KEY: Peptide
    ( B ) LOCATION: 2
    ( D ) OTHER INFORMATION: /product="D-tryptophyl"

( i x ) FEATURE:
    ( A ) NAME/KEY: Peptide
    ( B ) LOCATION: 3
    ( D ) OTHER INFORMATION: /product="D-tryptophyl"

( i x ) FEATURE:
    ( A ) NAME/KEY: Peptide
    ( B ) LOCATION: 4
    ( D ) OTHER INFORMATION: /product="L-4-carboxyglutamyl amide dimethyl ester"

( x i ) SEQUENCE DESCRIPTION: SEQ ID NO:23:

Xaa Xaa Xaa Xaa
1

( 2 ) INFORMATION FOR SEQ ID NO:24:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-tryptophyl"

( i x ) FEATURE:
    ( A ) NAME/KEY: Peptide
    ( B ) LOCATION: 2
    ( D ) OTHER INFORMATION: /product="D-tryptophyl"

( i x ) FEATURE:
  ( A ) NAME/KEY: Peptide
  ( B ) LOCATION: 3
  ( D ) OTHER INFORMATION: /product="D-p-chlorophenylalanyl"

( i x ) FEATURE:
  ( A ) NAME/KEY: Peptide
  ( B ) LOCATION: 4
  ( D ) OTHER INFORMATION: /product="L-4-carboxyglutamyl amide dimethyl ester"

( x i ) SEQUENCE DESCRIPTION: SEQ ID NO:24:

Xaa Xaa Xaa Xaa
1

( 2 ) INFORMATION FOR SEQ ID NO:25:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-tryptophyl"

( i x ) FEATURE:
    ( A ) NAME/KEY: Peptide
    ( B ) LOCATION: 2
    ( D ) OTHER INFORMATION: /product="D-tryptophyl"

( i x ) FEATURE:
    ( A ) NAME/KEY: Peptide
    ( B ) LOCATION: 3
    ( D ) OTHER INFORMATION: /product="L-p-chlorophenylalanyl"

( i x ) FEATURE:
    ( A ) NAME/KEY: Peptide
    ( B ) LOCATION: 4
    ( D ) OTHER INFORMATION: /product="L-4-carboxyglutamyl amide dimethyl ester"

( x i ) SEQUENCE DESCRIPTION: SEQ ID NO:25:

Xaa Xaa Xaa Xaa
1

( 2 ) INFORMATION FOR SEQ ID NO:26:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /product="D-tryptophyl"

( i x ) FEATURE:
    ( A ) NAME/KEY: Peptide
    ( B ) LOCATION: 2
    ( D ) OTHER INFORMATION: /product="D-methioninyl"

( i x ) FEATURE:
    ( A ) NAME/KEY: Peptide
    ( B ) LOCATION: 3
    ( D ) OTHER INFORMATION: /product="D-phenylalanyl"

( i x ) FEATURE:

( A ) NAME/KEY: Peptide
            ( B ) LOCATION: 4
            ( D ) OTHER INFORMATION: /product="L-4-carboxyglutamyl
                amide dimethyl ester"

( x i ) SEQUENCE DESCRIPTION: SEQ ID NO:26:

Xaa  Xaa  Xaa  Xaa
    1

( 2 ) INFORMATION FOR SEQ ID NO:27:

( i ) SEQUENCE CHARACTERISTICS:
            ( A ) LENGTH: 4 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Peptide
            ( B ) LOCATION: 1
            ( D ) OTHER INFORMATION: /product="D-tryptophyl"

( i x ) FEATURE:
            ( A ) NAME/KEY: Peptide
            ( B ) LOCATION: 2
            ( D ) OTHER INFORMATION: /product="D-methioninyl"

( i x ) FEATURE:
            ( A ) NAME/KEY: Peptide
            ( B ) LOCATION: 3
            ( D ) OTHER INFORMATION: /product="D-tryptophyl"

( i x ) FEATURE:
            ( A ) NAME/KEY: Peptide
            ( B ) LOCATION: 4
            ( D ) OTHER INFORMATION: /product="L-4-carboxyglutamyl
                amide dimethyl ester"

( x i ) SEQUENCE DESCRIPTION: SEQ ID NO:27:

Xaa  Xaa  Xaa  Xaa
    1

( 2 ) INFORMATION FOR SEQ ID NO:28:

( i ) SEQUENCE CHARACTERISTICS:
            ( A ) LENGTH: 4 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Peptide
            ( B ) LOCATION: 1
            ( D ) OTHER INFORMATION: /product="D-tryptophyl"

( i x ) FEATURE:
            ( A ) NAME/KEY: Peptide
            ( B ) LOCATION: 2
            ( D ) OTHER INFORMATION: /product="D-methioninyl"

( i x ) FEATURE:
            ( A ) NAME/KEY: Peptide
            ( B ) LOCATION: 3
            ( D ) OTHER INFORMATION: /product="D-p-chlorophenylalanyl"

( i x ) FEATURE:
            ( A ) NAME/KEY: Peptide
            ( B ) LOCATION: 4
            ( D ) OTHER INFORMATION: /product="L-4-carboxyglutamyl
                amide dimethyl ester"

( x i ) SEQUENCE DESCRIPTION: SEQ ID NO:28:

Xaa  Xaa  Xaa  Xaa
          1

( 2 ) INFORMATION FOR SEQ ID NO:29:

( i ) SEQUENCE CHARACTERISTICS:
                  ( A ) LENGTH: 4 amino acids
                  ( B ) TYPE: amino acid
                  ( C ) STRANDEDNESS: single
                  ( D ) TOPOLOGY: linear ( i i ) MOLECULE TYPE: peptide ( i x ) FEATURE:
                  ( A ) NAME/KEY: Peptide
                  ( B ) LOCATION: 1
                  ( D ) OTHER INFORMATION: /product="D-tryptophyl"

( i x ) FEATURE:
                  ( A ) NAME/KEY: Peptide
                  ( B ) LOCATION: 2
                  ( D ) OTHER INFORMATION: /product="D-methioninyl"

( i x ) FEATURE:
                  ( A ) NAME/KEY: Peptide
                  ( B ) LOCATION: 3
                  ( D ) OTHER INFORMATION: /product="L-p-chlorophenylalanyl"

( i x ) FEATURE:
                  ( A ) NAME/KEY: Peptide
                  ( B ) LOCATION: 4
                  ( D ) OTHER INFORMATION: /product="L-4-carboxyglutamyl
                         amide dimethyl ester"

( x i ) SEQUENCE DESCRIPTION: SEQ ID NO:29:

Xaa  Xaa  Xaa  Xaa
          1

( 2 ) INFORMATION FOR SEQ ID NO:30:

( i ) SEQUENCE CHARACTERISTICS:
                  ( A ) LENGTH: 4 amino acids
                  ( B ) TYPE: amino acid
                  ( C ) STRANDEDNESS: single
                  ( D ) TOPOLOGY: linear ( i i ) MOLECULE TYPE: peptide ( i x ) FEATURE:
                  ( A ) NAME/KEY: Peptide
                  ( B ) LOCATION: 1
                  ( D ) OTHER INFORMATION: /product="D-tryptophyl"

( i x ) FEATURE:
                  ( A ) NAME/KEY: Peptide
                  ( B ) LOCATION: 3
                  ( D ) OTHER INFORMATION: /product="D-phenylalanyl"

( i x ) FEATURE:
                  ( A ) NAME/KEY: Peptide
                  ( B ) LOCATION: 4
                  ( D ) OTHER INFORMATION: /product="L-4-carboxyglutamyl
                         amide dimethyl ester"

( x i ) SEQUENCE DESCRIPTION: SEQ ID NO:30:

Xaa  Trp  Xaa  Xaa
          1

( 2 ) INFORMATION FOR SEQ ID NO:31:

( i ) SEQUENCE CHARACTERISTICS:
                  ( A ) LENGTH: 4 amino acids
                  ( B ) TYPE: amino acid
                  ( C ) STRANDEDNESS: single (D) TOPOLOGY: linear (ii) MOLECULE TYPE: peptide (ix) FEATURE:
(A) NAME/KEY: Peptide
(B) LOCATION: 1
(D) OTHER INFORMATION: /product="D-tryptophyl"

(ix) FEATURE:
(A) NAME/KEY: Peptide
(B) LOCATION: 3
(D) OTHER INFORMATION: /product="D-tryptophyl"

(ix) FEATURE:
(A) NAME/KEY: Peptide
(B) LOCATION: 4
(D) OTHER INFORMATION: /product="L-4-carboxyglutamyl amide dimethyl ester"

(xi) SEQUENCE DESCRIPTION: SEQ ID NO:31:

Xaa Trp Xaa Xaa
1

(2) INFORMATION FOR SEQ ID NO:32:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1
(D) OTHER INFORMATION: /product="D-tryptophyl"

(ix) FEATURE:
(A) NAME/KEY: Peptide
(B) LOCATION: 3
(D) OTHER INFORMATION: /product="D-p-chlorophenylalanyl"

(ix) FEATURE:
(A) NAME/KEY: Peptide
(B) LOCATION: 4
(D) OTHER INFORMATION: /product="L-4-carboxyglutamyl amide dimethyl ester"

(xi) SEQUENCE DESCRIPTION: SEQ ID NO:32:

Xaa Trp Xaa Xaa
1

(2) INFORMATION FOR SEQ ID NO:33:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1
(D) OTHER INFORMATION: /product="D-tryptophyl"

(ix) FEATURE:
(A) NAME/KEY: Peptide
(B) LOCATION: 3
(D) OTHER INFORMATION: /product="L-p-chlorophenylalanyl"

(ix) FEATURE:
(A) NAME/KEY: Peptide (B) LOCATION: 4
(D) OTHER INFORMATION: /product="L-4-carboxyglutamyl amide dimethyl ester"

(xi) SEQUENCE DESCRIPTION: SEQ ID NO:33:

Xaa Trp Xaa Xaa
1